US012778135B2

(12) United States Patent
Mitsui et al.

(10) Patent No.: US 12,778,135 B2
(45) Date of Patent: Nov. 3, 2026

(54) PROTEIN HAVING PEPTIDOGLYCAN-DEGRADING ACTIVITY AND DNA ENCODING PROTEIN, MICROORGANISM DEGRADING PREPARATION AND METHOD FOR DEGRADING MICROORGANISM

(71) Applicants: SUMITOMO CHEMICAL COMPANY, LIMITED, Tokyo (JP); KATAOKA BIO LABORATORY CO., LTD., Isehara (JP)

(72) Inventors: Tomokazu Mitsui, Osaka (JP); Akiho Harima, Osaka (JP); Yusuke Onishi, Osaka (JP)

(73) Assignees: SUMITOMO CHEMICAL COMPANY, LIMITED, Tokyo (JP); KATAOKA BIO LABORATORY CO., LTD., Isehara (JP)

( * ) Notice: Subject to any disclaimer, the term of this patent is extended or adjusted under 35 U.S.C. 154(b) by 532 days.

(21) Appl. No.: 17/914,652

(22) PCT Filed: Mar. 24, 2021

(86) PCT No.: PCT/JP2021/012344
§ 371 (c)(1),
(2) Date: Sep. 26, 2022

(87) PCT Pub. No.: WO2021/193749
PCT Pub. Date: Sep. 30, 2021

(65) Prior Publication Data

US 2023/0146232 A1 May 11, 2023

(30) Foreign Application Priority Data

Mar. 26, 2020 (JP) ................................ 2020-056455

(51) Int. Cl.

| | |
|---|---|
| ***A01N 63/50*** | (2020.01) |
| ***C12N 9/36*** | (2006.01) |
| ***C12N 9/48*** | (2006.01) |
| ***C12N 15/52*** | (2006.01) |
| ***C12N 15/70*** | (2006.01) |

(52) U.S. Cl.
CPC ........... *A01N 63/50* (2020.01); *C12N 9/2462* (2013.01); *C12N 9/48* (2013.01); *C12N 15/52* (2013.01); *C12N 15/70* (2013.01)

(58) Field of Classification Search
CPC ........ A01N 63/50; C12N 9/2462; C12N 9/48; C12N 15/52; C12N 15/70; C12N 1/205; C12N 9/80; C12N 15/06; C02F 11/147; C02F 2303/06; C12R 2001/01; A01P 1/00; C12Y 302/01017; C12Y 305/01028
See application file for complete search history.

(56) References Cited

U.S. PATENT DOCUMENTS

| | | | |
|---|---|---|---|
| 11,959,111 B2 * | 4/2024 | Oehlenschlaeger | C11D 3/38636 |
| 12,241,055 B2 * | 3/2025 | Mitsui | C02F 11/02 |
| 2012/0171188 A1 | 7/2012 | Loessner et al. | |
| 2012/0195872 A1 | 8/2012 | Miller | |
| 2021/0380932 A1 * | 12/2021 | Mitsui | C12N 1/205 |

FOREIGN PATENT DOCUMENTS

| | | | |
|---|---|---|---|
| JP | 2-22000 A | 1/1990 | |
| JP | 2007-268502 A | 10/2007 | |
| JP | 2017-51890 A | 3/2017 | |
| WO | WO 2020/067555 A1 | 4/2020 | |
| WO | WO-2020127796 A2 * | 6/2020 | C11D 3/38636 |

OTHER PUBLICATIONS

Abanes-De Mello A, Sun YL, Aung S, Pogliano K. A cytoskeleton-like role for the bacterial cell wall during engulfment of the *Bacillus subtilis* forespore. Genes & Development. Dec. 15, 2002;16(24):3253-64. (Year: 2002).*

Wang Q, Xie N, Qin Y, Shen N, Zhu J, Mi H, Huang R. *Tumebacillus flagellatus* sp. nov., an Î±-amylase/pullulanase-producing bacterium isolated from cassava wastewater. International Journal of Systematic and Evolutionary Microbiology. Sep. 2013;63(Pt_9):3138-42. (Year: 2013).*

Pazos, M., Peters, K. (2019). Peptidoglycan. In: Kuhn, A. (eds) Bacterial Cell Walls and Membranes . Subcellular Biochemistry, vol. 92. Springer, Cham. (Year: 2019).*

Shen, Z., Ruan, Y., Xue, C. et al. Soils naturally suppressive to banana Fusarium wilt disease harbor unique bacterial communities. Plant Soil 393, 21-33 (Year: 2015).*

Garcia-Cano I, Campos-Gomez M, Contreras-Cruz M, et al. Expression, purification, and characterization of a bifunctional 99-kDa peptidoglycan hydrolase from Pediococcus acidilactici ATCC 8042. Applied microbiology and biotechnology. Oct. 2015;99:8563-73. (Year: 2015).*

Liu W, Zhong X, Cheng L, Wang J, Sun Y, Deng Y, Zhang Z. Cellular and compositional insight into the sludge dewatering process using enzyme treatment. Environmental Science and Pollution Research. Oct. 2018;25:28942-53. (Year: 2018).*

(Continued)

*Primary Examiner* — Sharmila G Landau
*Assistant Examiner* — Emily F Eix
(74) *Attorney, Agent, or Firm* — Birch, Stewart, Kolasch & Birch, LLP

(57) ABSTRACT

Provided is a protein derived from *Tumebacillus* sp. NITE BP-02779 and having peptidoglycan-degrading activity. Provided is a protein comprising the amino acid sequence at positions 1 to 164 of SEQ ID NO: 2 or the amino acid sequence at positions 1 to 493 of SEQ ID NO: 4, or the amino acid sequences with a substitution, deletion, insertion, or addition of 1 to 10 amino acid residues, or an amino acid sequence having 90% or more identity to the amino acid sequences, and having peptidoglycan-degrading activity.

7 Claims, 4 Drawing Sheets

Specification includes a Sequence Listing.

(56) References Cited

OTHER PUBLICATIONS

"Fiscal year of Heisei 30, Report on current status of industrial waste treatment, Results of Heisei 28 (Digest edition)", Minister's Secretariat, Ministry of the Environment Waste Management and Recycling Department, Mar. 2019, 98 total pages.
Accession No. AOA074LX93, Database Uniprot [online], Oct. 1, 2014, retrieval date May 10, 2021, <https://www.uniprot.org/uniprot/AOA074LX93.txt?version=l> sequence. 1 page.
Accession No. AOA316D9Z5, Database Uniprot [online], Oct. 10, 2018, retrieval date May 10, 2021, <https://www.uniprot.org/uniprot/AOA316D9Z5.txt?version=l> sequence. 1 page.
International Search Report (PCT/ISA/210) issued in PCT/JP2021/012344, dated May 25, 2021.
Yamamoto, "Combustion Technology of the Sewage", Journal of the Combustion Society of Japan, vol. 53, No. 164, 2011, pp. 91-96.
Goeker, "Transglycosylase-like protein with SLT domain", Database Gen Bank [Online], XP093226817, Database accession No. A0A316DTK5, Oct. 10, 2018, 1 page total.
Wang et al., "N-acetylmuramoyl-L-alanine amidase domain-containing protein," Database Gen Bank [Online], XP093226829, Database accession No. A0A074LP21, Oct. 1, 2014, 2 pages total.
Wang et al., "*Tumebacillus flagellatus* sp. nov., an α-amylase/pullulanase-producing bacterium isolated from cassava wastewater," International Journal of Systematic and Evolutionary Microbiology, vol. 63, 2013, pp. 3138-3142.
Garcia-Cano et al., "Expression, purification, and characterization of a bifunctional 99-kDa peptidoglycan hydrolase from Pediococcus acidilactici ATCC 8042," Applied Microbiology and Biotechnology, vol. 99, 2015, pp. 8563-8573.
Goeker, "Stage II sporulation protein [Tumebacillus permanentifrigoris]," GenBank, Accession No. PWK13453.1, May 22, 2018, 1 page total.
"Hypothetical protein [Tumebacillus permanentifrigoris]," NCBI Reference Sequence, Accession No. WP_109688727.1, May 26, 2018, 1 page total.

* cited by examiner

SEQUENCE LISTING

```
<160> NUMBER OF SEQ ID NOS: 26

<210> SEQ ID NO 1
<211> LENGTH: 699
<212> TYPE: DNA
<213> ORGANISM: Tumebacillus sp. NITE BP-02779
<220> FEATURE:
<221> NAME/KEY: CDS
<222> LOCATION: (1)..(696)
<220> FEATURE:
<221> NAME/KEY: mat_peptide
<222> LOCATION: (205)..(696)

<400> SEQUENCE: 1

atg aaa aaa gca tct gca ctg ctg ttg atg aca gct gca atg tcc ctc        48
Met Lys Lys Ala Ser Ala Leu Leu Leu Met Thr Ala Ala Met Ser Leu
            -65                 -60                 -55

gtg gca acc tcc gcg atg gca acc ccg gct gtg aag gaa gtc aaa caa        96
Val Ala Thr Ser Ala Met Ala Thr Pro Ala Val Lys Glu Val Lys Gln
        -50                 -45                 -40

aaa gac ggc tcc gtt cgt ctc gac gtt gca gaa cgt ccg tcc aac ggc       144
Lys Asp Gly Ser Val Arg Leu Asp Val Ala Glu Arg Pro Ser Asn Gly
    -35                 -30                 -25

acc ccg gaa gca caa caa ggc acg aaa ctc gtg gtt gac ccg caa ggc       192
Thr Pro Glu Ala Gln Gln Gly Thr Lys Leu Val Val Asp Pro Gln Gly
-20                 -15                 -10                 -5

gtg acc gca gca gcg gcg tac acc aag ccg tcc acg atc cgc gtc ggg       240
Val Thr Ala Ala Ala Ala Tyr Thr Lys Pro Ser Thr Ile Arg Val Gly
            -1  1               5                   10

att cgt gcg aac aac aac acc gcg aac ccg atc ggt tcc gta tcg gtt       288
Ile Arg Ala Asn Asn Asn Thr Ala Asn Pro Ile Gly Ser Val Ser Val
        15                  20                  25

gtt ccg tgg tat gac tac aac atc gac gtg ctc ccg aac gag tgg atc       336
Val Pro Trp Tyr Asp Tyr Asn Ile Asp Val Leu Pro Asn Glu Trp Ile
    30                  35                  40

ggc tct tgg ccg gca caa tcg ctc aac gca ggc gcg atc gca gta aaa       384
Gly Ser Trp Pro Ala Gln Ser Leu Asn Ala Gly Ala Ile Ala Val Lys
45                  50                  55                  60

atg tac gct tgg tat cat atc ctt cat ccg aaa tac tcc acc tgt gac       432
Met Tyr Ala Trp Tyr His Ile Leu His Pro Lys Tyr Ser Thr Cys Asp
                65                  70                  75

gtt gat aac acg gta aac tcc caa gtt tac aaa gca ggc tcc cgc tat       480
Val Asp Asn Thr Val Asn Ser Gln Val Tyr Lys Ala Gly Ser Arg Tyr
            80                  85                  90

agc aac acc acg acc gct gtt gat aac atg tcc ggc atc ggc atc ctc       528
Ser Asn Thr Thr Thr Ala Val Asp Asn Met Ser Gly Ile Gly Ile Leu
        95                  100                 105

aaa agc ggc gtg atg ttc gaa acc caa tac cgt gct ggc tcg tac gat       576
Lys Ser Gly Val Met Phe Glu Thr Gln Tyr Arg Ala Gly Ser Tyr Asp
    110                 115                 120

tcc tcg atc ccg ggc acg aac att atg tcc caa aac ggt acc cac tac       624
Ser Ser Ile Pro Gly Thr Asn Ile Met Ser Gln Asn Gly Thr His Tyr
125                 130                 135                 140

tac gca gac caa ggc aaa act tgg tct tgg atg acg aac tac tac tac       672
Tyr Ala Asp Gln Gly Lys Thr Trp Ser Trp Met Thr Asn Tyr Tyr Tyr
                145                 150                 155

ccg ggt tcc gca caa ttc acc tac taa                                   699
Pro Gly Ser Ala Gln Phe Thr Tyr
            160


<210> SEQ ID NO 2
<211> LENGTH: 232
```

```
<212> TYPE: PRT
<213> ORGANISM: Tumebacillus sp. NITE BP-02779

<400> SEQUENCE: 2

Met Lys Lys Ala Ser Ala Leu Leu Leu Met Thr Ala Ala Met Ser Leu
            -65                 -60                 -55

Val Ala Thr Ser Ala Met Ala Thr Pro Ala Val Lys Glu Val Lys Gln
        -50                 -45                 -40

Lys Asp Gly Ser Val Arg Leu Asp Val Ala Glu Arg Pro Ser Asn Gly
    -35                 -30                 -25

Thr Pro Glu Ala Gln Gln Gly Thr Lys Leu Val Val Asp Pro Gln Gly
-20                 -15                 -10                 -5

Val Thr Ala Ala Ala Ala Tyr Thr Lys Pro Ser Thr Ile Arg Val Gly
            -1  1               5                   10

Ile Arg Ala Asn Asn Asn Thr Ala Asn Pro Ile Gly Ser Val Ser Val
        15                  20                  25

Val Pro Trp Tyr Asp Tyr Asn Ile Asp Val Leu Pro Asn Glu Trp Ile
    30                  35                  40

Gly Ser Trp Pro Ala Gln Ser Leu Asn Ala Gly Ala Ile Ala Val Lys
45                  50                  55                  60

Met Tyr Ala Trp Tyr His Ile Leu His Pro Lys Tyr Ser Thr Cys Asp
                65                  70                  75

Val Asp Asn Thr Val Asn Ser Gln Val Tyr Lys Ala Gly Ser Arg Tyr
            80                  85                  90

Ser Asn Thr Thr Thr Ala Val Asp Asn Met Ser Gly Ile Gly Ile Leu
        95                  100                 105

Lys Ser Gly Val Met Phe Glu Thr Gln Tyr Arg Ala Gly Ser Tyr Asp
    110                 115                 120

Ser Ser Ile Pro Gly Thr Asn Ile Met Ser Gln Asn Gly Thr His Tyr
125                 130                 135                 140

Tyr Ala Asp Gln Gly Lys Thr Trp Ser Trp Met Thr Asn Tyr Tyr Tyr
                145                 150                 155

Pro Gly Ser Ala Gln Phe Thr Tyr
            160


<210> SEQ ID NO 3
<211> LENGTH: 1566
<212> TYPE: DNA
<213> ORGANISM: Tumebacillus sp. NITE BP-02779
<220> FEATURE:
<221> NAME/KEY: CDS
<222> LOCATION: (1)..(1563)
<220> FEATURE:
<221> NAME/KEY: mat_peptide
<222> LOCATION: (85)..(1563)

<400> SEQUENCE: 3

atg aaa aaa act tgg gtt tcg gtc ctt gcg acc acc gcg ctg acg ctg       48
Met Lys Lys Thr Trp Val Ser Val Leu Ala Thr Thr Ala Leu Thr Leu
            -25                 -20                 -15

tcg gtt ggc agc gta tac gcg caa cct gcg cat gca gaa cag tct acc       96
Ser Val Gly Ser Val Tyr Ala Gln Pro Ala His Ala Glu Gln Ser Thr
        -10                 -5                  -1  1

aaa caa tcg gtc gcc act gca ccc gtt ctg gaa agc gca ttc aca tcc      144
Lys Gln Ser Val Ala Thr Ala Pro Val Leu Glu Ser Ala Phe Thr Ser
5                   10                  15                  20

gct gcg aag gaa ttt ggc gtt ccg aag gac ctg ctg atg gcg atc tcc      192
Ala Ala Lys Glu Phe Gly Val Pro Lys Asp Leu Leu Met Ala Ile Ser
                25                  30                  35
```

```
tat agc gag tcg cgc tgg cag atc gcg cca gag gaa gcc cgc act agc      240
Tyr Ser Glu Ser Arg Trp Gln Ile Ala Pro Glu Glu Ala Arg Thr Ser
            40                  45                  50

tcg gag ccg gat aaa aac aac ggc aag ggt ctg atg cac ctc cag gac      288
Ser Glu Pro Asp Lys Asn Asn Gly Lys Gly Leu Met His Leu Gln Asp
        55                  60                  65

aac tcc ttc aaa aaa ggt ctg agc gaa gca gca aaa gcg ctc ggc gtt      336
Asn Ser Phe Lys Lys Gly Leu Ser Glu Ala Ala Lys Ala Leu Gly Val
    70                  75                  80

tcc aaa aaa cag atg gaa gat gac atc caa ttg aat atc cgc ggc ggt      384
Ser Lys Lys Gln Met Glu Asp Asp Ile Gln Leu Asn Ile Arg Gly Gly
85                  90                  95                  100

gcc tac ctg ctg tca aaa gca caa aaa gac ctc ggc aag acg ctc acc      432
Ala Tyr Leu Leu Ser Lys Ala Gln Lys Asp Leu Gly Lys Thr Leu Thr
                105                 110                 115

gcc aac gcg aac gat tgg tac gaa gcg gtc gct tcc ttc gaa gga gcc      480
Ala Asn Ala Asn Asp Trp Tyr Glu Ala Val Ala Ser Phe Glu Gly Ala
            120                 125                 130

aag gac aag gac ctc ggc gca ctg ttc gct gac gaa gtg tac cgt gtg      528
Lys Asp Lys Asp Leu Gly Ala Leu Phe Ala Asp Glu Val Tyr Arg Val
        135                 140                 145

ctg aag gaa ggc acg gcg ctg gcg atc tct ggc ggc acg ctg acg ctc      576
Leu Lys Glu Gly Thr Ala Leu Ala Ile Ser Gly Gly Thr Leu Thr Leu
    150                 155                 160

gac ccg aac aaa tcg atc gct cca gcc aaa ggc tcc tac gca ggc ttg      624
Asp Pro Asn Lys Ser Ile Ala Pro Ala Lys Gly Ser Tyr Ala Gly Leu
165                 170                 175                 180

atc cca ggt ggt acg aac tac gga ctg acc ccg gac tac tcc ggc gcg      672
Ile Pro Gly Gly Thr Asn Tyr Gly Leu Thr Pro Asp Tyr Ser Gly Ala
                185                 190                 195

atc tgg aac ccg gcc agc tcg tcg aac tat gcg gtt gcc tcc cgc ccc      720
Ile Trp Asn Pro Ala Ser Ser Ser Asn Tyr Ala Val Ala Ser Arg Pro
            200                 205                 210

aca tcg aac gcg atc acc tcg gtc atc atc cat gac acc gag ggt tcc      768
Thr Ser Asn Ala Ile Thr Ser Val Ile Ile His Asp Thr Glu Gly Ser
        215                 220                 225

tac tcc gga tcg atc aac tgg ttc aaa gac ccg gcg gcg caa gtt tcc      816
Tyr Ser Gly Ser Ile Asn Trp Phe Lys Asp Pro Ala Ala Gln Val Ser
    230                 235                 240

gcg cac tac atc gtc cgt tcc tcc gac ggg caa atc acg cag ttg gtc      864
Ala His Tyr Ile Val Arg Ser Ser Asp Gly Gln Ile Thr Gln Leu Val
245                 250                 255                 260

caa gac aag gac atc gcg tgg cat gcg cgc acc ttc aac acc aac ggc      912
Gln Asp Lys Asp Ile Ala Trp His Ala Arg Thr Phe Asn Thr Asn Gly
                265                 270                 275

atc ggc atc gag cac gag ggc tat gcg gcc caa acc ggc tgg tac acc      960
Ile Gly Ile Glu His Glu Gly Tyr Ala Ala Gln Thr Gly Trp Tyr Thr
            280                 285                 290

gat gcg atg tac act gca tcg gcg gcg ctc acc cgt gca gtc tgt ctc     1008
Asp Ala Met Tyr Thr Ala Ser Ala Ala Leu Thr Arg Ala Val Cys Leu
        295                 300                 305

aaa tac aac atc ccg atg gac cgc gaa cac atc atg gca cac tct gaa     1056
Lys Tyr Asn Ile Pro Met Asp Arg Glu His Ile Met Ala His Ser Glu
    310                 315                 320

ctc tgg ggc aac gac cac acc gat ccg ggc gtg aac tgg gac tgg aac     1104
Leu Trp Gly Asn Asp His Thr Asp Pro Gly Val Asn Trp Asp Trp Asn
325                 330                 335                 340

aaa tac atg agc aaa gtc acc ggc gtc acg aaa aac tac gat gcc gtg     1152
Lys Tyr Met Ser Lys Val Thr Gly Val Thr Lys Asn Tyr Asp Ala Val
```

```
            345                 350                 355

ctg gtc gac aac aca gac gcc tcc tcc ggc ttc tcg ctg ggc ggc ccg     1200
Leu Val Asp Asn Thr Asp Ala Ser Ser Gly Phe Ser Leu Gly Gly Pro
            360                 365                 370

tcc cag tat tgg cat ccg acc gct ggc tac ggc atc cac aac cag atg     1248
Ser Gln Tyr Trp His Pro Thr Ala Gly Tyr Gly Ile His Asn Gln Met
        375                 380                 385

acc tac acg atg ggc aat ggc acc aac ccg atc tcc aac tac gcg acg     1296
Thr Tyr Thr Met Gly Asn Gly Thr Asn Pro Ile Ser Asn Tyr Ala Thr
    390                 395                 400

tgg aga ccg acg atc acg acc tcg ggc aac tac caa gtg aaa gtc ttc     1344
Trp Arg Pro Thr Ile Thr Thr Ser Gly Asn Tyr Gln Val Lys Val Phe
405                 410                 415                 420

atc ccg tcc aac ttc gcc gcg acc acc aac gcg aag tac gag atc cat     1392
Ile Pro Ser Asn Phe Ala Ala Thr Thr Asn Ala Lys Tyr Glu Ile His
                425                 430                 435

tac aac ggc ggc gtg atc acc aag acg atc tcc caa gcc gca tac tcc     1440
Tyr Asn Gly Gly Val Ile Thr Lys Thr Ile Ser Gln Ala Ala Tyr Ser
            440                 445                 450

aac caa tgg gtg agc ctc ggc acc tac agt ttt gca gcc ggc acc acc     1488
Asn Gln Trp Val Ser Leu Gly Thr Tyr Ser Phe Ala Ala Gly Thr Thr
        455                 460                 465

ggc tac gtc atg ttg ggt gac aac acc ggc gac aaa gcg tac gtc ggc     1536
Gly Tyr Val Met Leu Gly Asp Asn Thr Gly Asp Lys Ala Tyr Val Gly
    470                 475                 480

att gac ggc atg cgt ttc ctc gct caa taa
Ile Asp Gly Met Arg Phe Leu Ala Gln
485                 490


<210> SEQ ID NO 4
<211> LENGTH: 521
<212> TYPE: PRT
<213> ORGANISM: Tumebacillus sp. NITE BP-02779

<400> SEQUENCE: 4

Met Lys Lys Thr Trp Val Ser Val Leu Ala Thr Thr Ala Leu Thr Leu
            -25                 -20                 -15

Ser Val Gly Ser Val Tyr Ala Gln Pro Ala His Ala Glu Gln Ser Thr
        -10                 -5                  -1  1

Lys Gln Ser Val Ala Thr Ala Pro Val Leu Glu Ser Ala Phe Thr Ser
5                   10                  15                  20

Ala Ala Lys Glu Phe Gly Val Pro Lys Asp Leu Leu Met Ala Ile Ser
                25                  30                  35

Tyr Ser Glu Ser Arg Trp Gln Ile Ala Pro Glu Glu Ala Arg Thr Ser
            40                  45                  50

Ser Glu Pro Asp Lys Asn Asn Gly Lys Gly Leu Met His Leu Gln Asp
        55                  60                  65

Asn Ser Phe Lys Lys Gly Leu Ser Glu Ala Ala Lys Ala Leu Gly Val
    70                  75                  80

Ser Lys Lys Gln Met Glu Asp Asp Ile Gln Leu Asn Ile Arg Gly Gly
85                  90                  95                  100

Ala Tyr Leu Leu Ser Lys Ala Gln Lys Asp Leu Gly Lys Thr Leu Thr
                105                 110                 115

Ala Asn Ala Asn Asp Trp Tyr Glu Ala Val Ala Ser Phe Glu Gly Ala
            120                 125                 130

Lys Asp Lys Asp Leu Gly Ala Leu Phe Ala Asp Glu Val Tyr Arg Val
        135                 140                 145
```

```
Leu Lys Glu Gly Thr Ala Leu Ala Ile Ser Gly Gly Thr Leu Thr Leu
    150                 155                 160

Asp Pro Asn Lys Ser Ile Ala Pro Ala Lys Gly Ser Tyr Ala Gly Leu
165                 170                 175                 180

Ile Pro Gly Gly Thr Asn Tyr Gly Leu Thr Pro Asp Tyr Ser Gly Ala
                185                 190                 195

Ile Trp Asn Pro Ala Ser Ser Ser Asn Tyr Ala Val Ala Ser Arg Pro
            200                 205                 210

Thr Ser Asn Ala Ile Thr Ser Val Ile Ile His Asp Thr Glu Gly Ser
        215                 220                 225

Tyr Ser Gly Ser Ile Asn Trp Phe Lys Asp Pro Ala Ala Gln Val Ser
    230                 235                 240

Ala His Tyr Ile Val Arg Ser Ser Asp Gly Gln Ile Thr Gln Leu Val
245                 250                 255                 260

Gln Asp Lys Asp Ile Ala Trp His Ala Arg Thr Phe Asn Thr Asn Gly
                265                 270                 275

Ile Gly Ile Glu His Glu Gly Tyr Ala Ala Gln Thr Gly Trp Tyr Thr
            280                 285                 290

Asp Ala Met Tyr Thr Ala Ser Ala Ala Leu Thr Arg Ala Val Cys Leu
        295                 300                 305

Lys Tyr Asn Ile Pro Met Asp Arg Glu His Ile Met Ala His Ser Glu
    310                 315                 320

Leu Trp Gly Asn Asp His Thr Asp Pro Gly Val Asn Trp Asp Trp Asn
325                 330                 335                 340

Lys Tyr Met Ser Lys Val Thr Gly Val Thr Lys Asn Tyr Asp Ala Val
                345                 350                 355

Leu Val Asp Asn Thr Asp Ala Ser Ser Gly Phe Ser Leu Gly Gly Pro
            360                 365                 370

Ser Gln Tyr Trp His Pro Thr Ala Gly Tyr Gly Ile His Asn Gln Met
        375                 380                 385

Thr Tyr Thr Met Gly Asn Gly Thr Asn Pro Ile Ser Asn Tyr Ala Thr
    390                 395                 400

Trp Arg Pro Thr Ile Thr Thr Ser Gly Asn Tyr Gln Val Lys Val Phe
405                 410                 415                 420

Ile Pro Ser Asn Phe Ala Ala Thr Thr Asn Ala Lys Tyr Glu Ile His
                425                 430                 435

Tyr Asn Gly Gly Val Ile Thr Lys Thr Ile Ser Gln Ala Ala Tyr Ser
            440                 445                 450

Asn Gln Trp Val Ser Leu Gly Thr Tyr Ser Phe Ala Ala Gly Thr Thr
        455                 460                 465

Gly Tyr Val Met Leu Gly Asp Asn Thr Gly Asp Lys Ala Tyr Val Gly
    470                 475                 480

Ile Asp Gly Met Arg Phe Leu Ala Gln
485                 490
```

<210> SEQ ID NO 5
<211> LENGTH: 20
<212> TYPE: DNA
<213> ORGANISM: Artificial Sequence
<220> FEATURE:
<223> OTHER INFORMATION: 27F, primer for 16S rRNA cloning

<400> SEQUENCE: 5
agrgtttgat cmtggctcag 20

<210> SEQ ID NO 6
<211> LENGTH: 19
<212> TYPE: DNA
<213> ORGANISM: Artificial Sequence
<220> FEATURE:
<223> OTHER INFORMATION: 1492R, primer for 16S rRNA cloning

<400> SEQUENCE: 6
ggytaccttg ttacgactt 19

<210> SEQ ID NO 7
<211> LENGTH: 19
<212> TYPE: DNA
<213> ORGANISM: Artificial Sequence
<220> FEATURE:
<223> OTHER INFORMATION: 339F, primer for 16S rRNA sequencing

<400> SEQUENCE: 7
ctcctacggg aggcagcag 19

<210> SEQ ID NO 8
<211> LENGTH: 18
<212> TYPE: DNA
<213> ORGANISM: Artificial Sequence
<220> FEATURE:
<223> OTHER INFORMATION: 536R, primer for 16S rRNA sequencing

<400> SEQUENCE: 8
gtattaccgc ggctgctg 18

<210> SEQ ID NO 9
<211> LENGTH: 20
<212> TYPE: DNA
<213> ORGANISM: Artificial Sequence
<220> FEATURE:
<223> OTHER INFORMATION: 907F, primer for 16S rRNA sequencing

<400> SEQUENCE: 9
aaactyaaag gaattgacgg 20

<210> SEQ ID NO 10
<211> LENGTH: 1471
<212> TYPE: DNA
<213> ORGANISM: Tumebacillus sp. NITE BP-02779

<400> SEQUENCE: 10
acgaacgctg gcggcgtgcc taatacatgc aagtcgagcg gagtgtmgag agcttgctct 60
cwraggtcag cggcggacgg gtgagtaaca cgtgggtaac ctgcctggca gactgggata 120
acgcttggaa acgagtgcta ataccggata atctcttgga tcgcatggtc tgagagtaaa 180
aggagctttt gcttcactgc yagatggacc cgcggcgcat tagctagttg gtgaggtaat 240
ggctcaccaa ggcgacgatg cgtagccgac ctgagagggt gaccggccac actgggactg 300
agacacggcc cagactccta cgggaggcag cagtagggaa tcttccgcaa tgggcgcaag 360
cctgacggag caacgccgcg tgagtgatga aggccttcgg gttgtaaaac tctgtcttct 420
gtgaagaacc atcctgtgca gagaaagctc aggacctgac ggtaacagag gaggaagccc 480
cggctaacta cgtgccagca gccgcggtaa tacgtagggg gcaagcgttg tccggaatca 540
ctgggcgtaa agcgcgcgca ggcggtctct cacgtccggg gtgaaagccc agagctcaac 600
tctgggattg ccttggatac ggggagactt gaggatcgga gaggcaaggg gaattccacg 660
tgtagcggtg aaatgcgtag agatgtggag gaacacctgt ggcgaaggcg ccttgctggc 720

```
cgatttctga cgctgaggcg cgaaagcgtg gggagcaaac aggattagat accctggtag    780

tccacgccgt aaacgatgag tgctaggtgt tagggggccc accccttagt gccgaagcta    840

acgcattaag cactccgcct ggggagtacg gtcgcaagac tgaaactcaa aggaattgac    900

gggggcccgc acaagcagtg gagcatgtgg tttaattcga agcaacgcga agaaccttac    960

caagacttga catcccgctg accrctctag agatagagyt tcccttcggg gcagcggtga   1020

caggtggtgc atggttgtcg tcagctcgtg tcgtgagatg ttgggttaag tcccgcaacg   1080

agcgcaaccc ctatgttgtg ttgctaccat ttagttgagc acttacaaca gactgccggt   1140

gacaaaccgg aggaaggcgg ggatgacgtc aaatcatcat gccccttatg tcttgggcta   1200

cacacgtgct acaatggacg gtacaaaggg ttgcgaagcc gcgaggtgaa gccaatccca   1260

gaaagccgtt cgtagttcgg attgcaggct gcaactcgcc tgcatgaagc cggaattgct   1320

agtaatcgcg gatcagcatg ccgcggtgaa ttcgttcccg ggccttgtac acaccgcccg   1380

tcacaccatg ggagttggta acacccgaag tcggtgaggt aactgcttgc agagccagcc   1440

gcctaaggtg ggatcgataa ctggggtgaa g                                  1471
```

```
<210> SEQ ID NO 11
<211> LENGTH: 46
<212> TYPE: PRT
<213> ORGANISM: Tumebacillus sp. NITE BP-02779

<400> SEQUENCE: 11

Ala Asn Asn Asn Thr Ala Asn Pro Ile Gly Ser Val Ser Val Val Pro
1               5                   10                  15

Trp Tyr Asp Tyr Asn Ile Asp Val Leu Pro Asn Glu Trp Ile Gly Ser
            20                  25                  30

Trp Pro Ala Gln Ser Leu Asn Ala Gly Ala Ile Ala Val Lys
        35                  40                  45


<210> SEQ ID NO 12
<211> LENGTH: 11
<212> TYPE: PRT
<213> ORGANISM: Tumebacillus sp. NITE BP-02779

<400> SEQUENCE: 12

Met Tyr Ala Trp Tyr His Ile Leu His Pro Lys
1               5                   10


<210> SEQ ID NO 13
<211> LENGTH: 16
<212> TYPE: PRT
<213> ORGANISM: Tumebacillus sp. NITE BP-02779

<400> SEQUENCE: 13

Tyr Ser Thr Cys Asp Val Asp Asn Thr Val Asn Ser Gln Val Tyr Lys
1               5                   10                  15


<210> SEQ ID NO 14
<211> LENGTH: 18
<212> TYPE: PRT
<213> ORGANISM: Tumebacillus sp. NITE BP-02779

<400> SEQUENCE: 14

Tyr Ser Asn Thr Thr Thr Ala Val Asp Asn Met Ser Gly Ile Gly Ile
1               5                   10                  15

Leu Lys
```

<210> SEQ ID NO 15
<211> LENGTH: 10
<212> TYPE: PRT
<213> ORGANISM: Tumebacillus sp. NITE BP-02779

<400> SEQUENCE: 15

Ser Gly Val Met Phe Glu Thr Gln Tyr Arg
1 5 10

<210> SEQ ID NO 16
<211> LENGTH: 27
<212> TYPE: PRT
<213> ORGANISM: Tumebacillus sp. NITE BP-02779

<400> SEQUENCE: 16

Ala Gly Ser Tyr Asp Ser Ser Ile Pro Gly Thr Asn Ile Met Ser Gln
1 5 10 15

Asn Gly Thr His Tyr Tyr Ala Asp Gln Gly Lys
20 25

<210> SEQ ID NO 17
<211> LENGTH: 18
<212> TYPE: PRT
<213> ORGANISM: Tumebacillus sp. NITE BP-02779

<400> SEQUENCE: 17

Thr Trp Ser Trp Met Thr Asn Tyr Tyr Tyr Pro Gly Ser Ala Gln Phe
1 5 10 15

Thr Tyr

<210> SEQ ID NO 18
<211> LENGTH: 10
<212> TYPE: PRT
<213> ORGANISM: Tumebacillus sp. NITE BP-02779

<400> SEQUENCE: 18

Ala Ala Tyr Thr Lys Pro Ser Thr Ile Arg
1 5 10

<210> SEQ ID NO 19
<211> LENGTH: 31
<212> TYPE: DNA
<213> ORGANISM: Artificial Sequence
<220> FEATURE:
<223> OTHER INFORMATION: F primer for ID2839 cloning

<400> SEQUENCE: 19
atatacatat ggcgtacacc aagccgtcca c 31

<210> SEQ ID NO 20
<211> LENGTH: 31
<212> TYPE: DNA
<213> ORGANISM: Artificial Sequence
<220> FEATURE:
<223> OTHER INFORMATION: R primer for ID2839 cloning

<400> SEQUENCE: 20
ccctcgagtt agtaggtgaa ttgtgcggaa c 31

<210> SEQ ID NO 21
<211> LENGTH: 20
<212> TYPE: PRT
<213> ORGANISM: Artificial Sequence
<220> FEATURE:
<223> OTHER INFORMATION: His_Tb restriction site

<400> SEQUENCE: 21

Met Gly Ser Ser His His His His His His Ser Ser Gly Leu Val Pro
1               5                   10                  15

Arg Gly Ser His
            20

<210> SEQ ID NO 22
<211> LENGTH: 33
<212> TYPE: DNA
<213> ORGANISM: Artificial Sequence
<220> FEATURE:
<223> OTHER INFORMATION: F primer for ID1644 cloning

<400> SEQUENCE: 22
cgccatatgg aacagtctac caaacaatcg gtc 33

<210> SEQ ID NO 23
<211> LENGTH: 27
<212> TYPE: DNA
<213> ORGANISM: Artificial Sequence
<220> FEATURE:
<223> OTHER INFORMATION: R primer for ID1644 cloning

<400> SEQUENCE: 23
ccctcgagtt attgagcgag gaaacgc 27

<210> SEQ ID NO 24
<211> LENGTH: 35
<212> TYPE: DNA
<213> ORGANISM: Artificial Sequence
<220> FEATURE:
<223> OTHER INFORMATION: F primer for ID2839 cloning

<400> SEQUENCE: 24
aggagatata ccatggcggc gtacaccaag ccgtc 35

<210> SEQ ID NO 25
<211> LENGTH: 35
<212> TYPE: DNA
<213> ORGANISM: Artificial Sequence
<220> FEATURE:
<223> OTHER INFORMATION: R primer for ID2839 cloning

<400> SEQUENCE: 25
gtggtggtgc tcgagttagt aggtgaattg tgcgg 35

<210> SEQ ID NO 26
<211> LENGTH: 35
<212> TYPE: DNA
<213> ORGANISM: Artificial Sequence
<220> FEATURE:
<223> OTHER INFORMATION: F primer for ID2839 cloning

<400> SEQUENCE: 26
aggagatata ccatggcgta caccaagccg tccac 35

PROTEIN HAVING PEPTIDOGLYCAN-DEGRADING ACTIVITY AND DNA ENCODING PROTEIN, MICROORGANISM DEGRADING PREPARATION AND METHOD FOR DEGRADING MICROORGANISM

REFERENCE TO AN ELECTRONIC SEQUENCE LISTING

The contents of the electronic sequence listing (2022-09-26 _Sequence_Listing_ 0033-1708PUS1.txt; Size: 24,500 bytes; and Date of Creation: Sep. 26, 2022) is herein incorporated by reference in its entirety.

TECHNICAL FIELD

The present invention relates to a protein having peptidoglycan-degrading activity and a DNA encoding the protein, a microorganism degrading preparation and a method for degrading microorganisms.

BACKGROUND ART

When waste water is decontaminated by an activated sludge process, removed organic matters form flocks that contain microorganisms (bacteria) and sludge called excess sludge is generated. Excess sludge that is discharged from waste water treatment plants accounts for as much as 20% or more of the industrial wastes. Excess sludge is generally dewatered, dried, and then incinerated (NPL 1: Fiscal year of Heisei 30, Report on current status of industrial waste treatment, Results of Heisei 28 (Digest edition), NPL 2: YAMAMOTO Masayuki, "Combustion Technology of the Sewage", Journal of the Combustion Society of Japan, Combustion Society of Japan, 2011, Vol. 53, 164, p 91-96).

CITATION LIST

Non Patent Literature

NPL 1: "Fiscal year of Heisei 30, Report on current status of industrial waste treatment, Results of Heisei 28 (Digest edition)," [online], March, Heisei 31, Minister's Secretariat, Ministry of the Environment Waste Management and Recycling Department, [searched on March 17, Reiwa 2], Internet <URL:https://www.e-stat.go.jp/stat-search/file-download?statInfId=000031887949&fileKind=2>

NPL 2: YAMAMOTO Masayuki, "Combustion Technology of the Sewage", Journal of the Combustion Society of Japan, Combustion Society of Japan, 2011, Vol. 53, 164, p 91-96).

SUMMARY OF INVENTION

Technical Problem

However, since incineration treatment of excess sludge generates greenhouse gasses, it is required to reduce the volume of the excess sludge in consideration of the environment. As a method for reducing the volume of excess sludge, a method for degrading microorganisms composing the excess sludge is proposed.

The present invention has an object to provide a novel protein capable of degrading peptidoglycan and DNA encoding the protein, a microorganism degrading preparation and a method for degrading microorganisms.

Solution to Problem

The present invention relates to [1] to [11] exemplified below.

[1] A protein derived from *Tumebacillus* sp. NITE BP-02779 and having peptidoglycan-degrading activity.

[2] The protein according to [1], which is a secretory protein.

[3] A protein which is any one of the following proteins (A1) to (A3):

(A1) a protein comprising the amino acid sequence at positions 1 to 164 of SEQ ID NO: 2, and having peptidoglycan-degrading activity;

(A2) a protein comprising the amino acid sequence at positions 1 to 164 of SEQ ID NO: 2 with a substitution, deletion, insertion or addition of 1 to 10 amino acid residues, and having peptidoglycan-degrading activity; and (A3) a protein comprising an amino acid sequence having 90% or more identity to the amino acid sequence at positions 1 to 164 of SEQ ID NO: 2, and having peptidoglycan-degrading activity.

[4] The protein according to any one of [1] to [3], wherein the peptidoglycan-degrading activity is activity to degrade a glycosidic linkage between N-acetylmuramic acid and N-acetylglucosamine.

[5] A protein which is any one of the following proteins (a1) to (a4):

(a1) a protein consisting of the amino acid sequence at positions 1 to 164 of SEQ ID NO: 2;

(a2) a protein consisting of an amino acid sequence at positions 1 to 164 of SEQ ID NO: 2 with a substitution of Ala at position 1 with Met;

(a3) a protein consisting of an amino acid sequence at positions 1 to 164 of SEQ ID NO: 2 with a substitution of Ala at position 1 with Met and addition of the amino acid sequence represented by SEQ ID NO: 21 to the N-terminus of the Met; and (a4) a protein consisting of an amino acid sequence at positions 1 to 164 of SEQ ID NO: 2 with addition of Met to the N-terminus of Ala at position 1.

[6] A protein which is any one of the following proteins (B1) to (B3):

(B1) a protein comprising the amino acid sequence at positions 1 to 493 of SEQ ID NO: 4, and having peptidoglycan-degrading activity;

(B2) a protein comprising the amino acid sequence at positions 1 to 493 of SEQ ID NO: 4 with a substitution, deletion, insertion or addition of 1 to 10 amino acid residues, and having peptidoglycan-degrading activity; and (B3) a protein comprising an amino acid sequence having 90% or more identity to the amino acid sequence at positions 1 to 493 of SEQ ID NO: 4, and having peptidoglycan-degrading activity.

[7] The protein according to [1], [2] or [6], wherein the peptidoglycan-degrading activity is N-acetylmuramoyl-L-alanine amidase activity.

[8] A protein which is any one of the following proteins (b1) to (b4):

(b1) a protein consisting of the amino acid sequence at positions 1 to 493 of SEQ ID NO: 4;

(b2) a protein consisting of the amino acid sequence at positions 1 to 493 of SEQ ID NO: 4 with a substitution of Glu at position 1 with Met;

(b3) a protein consisting of the amino acid sequence at positions 1 to 493 of SEQ ID NO: 4 with a substitution of Glu at position 1 with Met and addition of the amino acid sequence represented by SEQ ID NO: 21 to the N-terminus of the Met; and (b4) a protein consisting of the amino acid sequence at positions 1 to 493 of SEQ ID NO: 4 with addition of Met to the N-terminus of Glu at position 1.

[9] A DNA encoding the protein according to any one of [1] to [8].

[10] A vector comprising the DNA according to [9].

[11] A transformant comprising the DNA according to [9] or the vector according to [10].

[12] A microorganism degrading preparation comprising at least one selected from the group consisting of the protein according to any one of [1] to [8], and the transformant according to [11] and a culture thereof.

[13] A method for degrading a microorganism, comprising allowing at least one selected from the group consisting of the protein according to any one of [1] to [8], and the transformant according to [11] and a culture thereof to act on a target microorganism.

Advantageous Effects of Invention

According to the present invention, a novel protein capable of degrading peptidoglycan and a DNA encoding the protein, a microorganism degrading preparation, and a method for degrading microorganisms can be provided.

DESCRIPTION OF EMBODIMENTS

Figure 1:
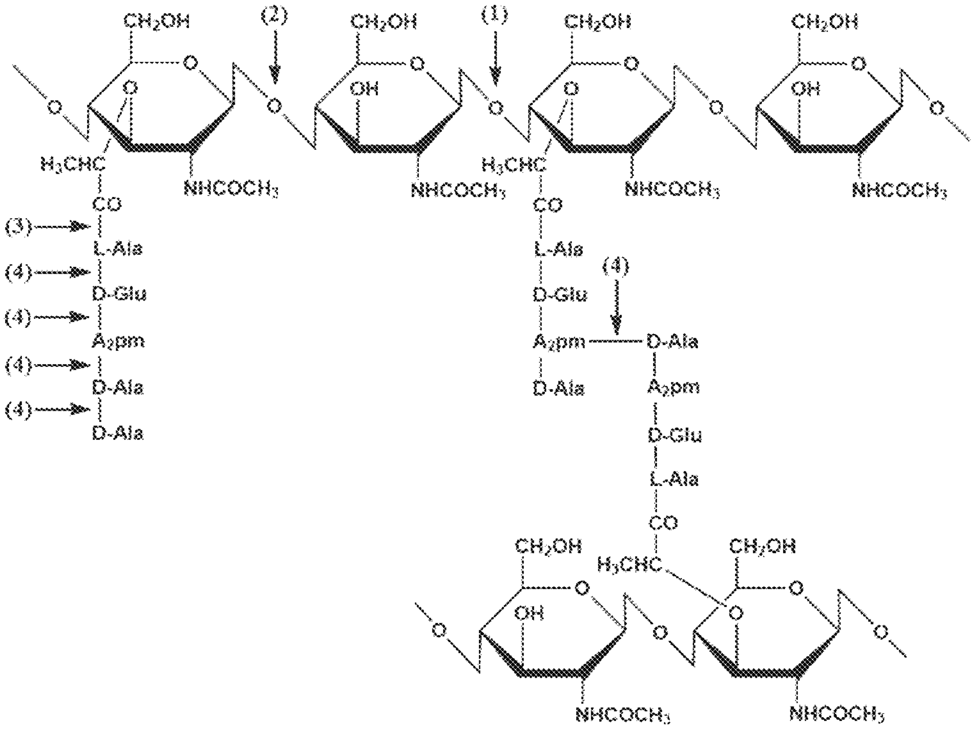
FIG. 1 shows the representative structure of a peptidoglycan and sites that can be cleaved by a peptidoglycan-degrading enzyme.

Hereinafter, embodiments to carry out the present invention are described in detail. The present invention is not limited to the following embodiments.

[Protein Derived from *Tumebacillus* sp. NITE BP-02779]

The protein according to an embodiment of the present invention is derived from *Tumebacillus* sp. NITE BP-02779 (hereinafter, also referred to as "NITE BP-02779"), and has peptidoglycan-degrading activity. The protein may be a synthesized protein or a purified or isolated protein. Whether or not a protein is the protein according to the present invention can be determined on the basis of the results of a method for identifying proteins and a method for measuring peptidoglycan-degrading activity described later. Such a protein derived from NITE BP-02779 and having peptidoglycan-degrading activity is capable of degrading a target microorganism, and thus can reduce the volume of excess sludge.

NITE BP-02779 is a bacterium that was internationally deposited on Sep. 11, 2018 to the Patent Microorganisms Depositary of the National Institute of Technology and Evaluation (NPMD, address: #122, 2-5-8 Kazusakamatari, Kisarazu-shi, Chiba 292-0818, JAPAN), for which the receipt of the original deposit and the certificate concerning survival were issued on Sep. 26, 2018. NITE BP-02779 is considered to be a new species of bacteria of the genus *Tumebacillus*. NITE BP-02779 is capable of degrading various target microorganisms including *Bacillus, Micrococcus, Staphylococcus* etc., and excess sludge, and thus is useful in treatment of excess sludge. Mycological characteristics of NITE BP-02779 will be shown in Tables 1 to 4 of Examples to be described later. NITE BP-02779 is a bacterium having a 16S rRNA gene comprising the nucleotide sequence represented by SEQ ID NO: 10.

The expression "derived from NITE BP-02779" may mean that a substance is synthesized or generated by NITE BP-02779 or based on the genomic sequence of NITE BP-02779. For example, the expression may mean that a substance is synthesized or generated artificially or within the cells of another organism based on the genomic sequence of NITE BP-02779. Examples of such a substance derived from NITE BP-02779 include biomolecules such as proteins, nucleic acids and sugars and metabolites. These products may be localized within cells after production or may be secreted extracellularly.

Examples of a method for investigating if a protein is such a protein derived from NITE BP-02779 include the following method. First, the genomic sequence of NITE BP-02779 is decoded by a next-generation sequencer. An adaptor sequence is trimmed from the thus obtained nucleotide sequence, and then de novo assembly is performed. Scaffold sequences obtained by de novo assembly are analyzed, gene region prediction and annotation are performed, and then a protein database for mass spectrometry is prepared. Next, a target protein is subjected to mass spectrometry and then the result is checked against the above protein database, so that if the target protein is a protein derived from NITE BP-02779 can be determined.

Another method for investigating if a protein is derived from NITE BP-02779 may involve decoding the amino acid sequence of a target protein by an amino acid sequencer, and then checking the result against the above protein database.

The protein derived from NITE BP-02779 and having peptidoglycan-degrading activity is preferably a secretory protein. A secretory protein can function extracellularly. In order to reduce the volume of excess sludge, it is useful for such a protein having peptidoglycan-degrading activity to have peptidoglycan-degrading activity in an extracellular environment. A secretory protein having peptidoglycan-degrading activity may be collected from the culture supernatant of cells producing the protein or collected by disrupting cells producing the protein.

Peptidoglycan is a molecule wherein polysaccharides composed of alternating N-acetylglucosamine (GlcNAc) and N-acetylmuramic acid (MurNAc) joined by β1,4 linkages are cross-linked via oligopeptides. FIG. 1 shows the representative structure of a peptidoglycan. The term "peptidoglycan-degrading activity" refers to a state in which a reaction of converting peptidoglycan into two or more types of substances is accelerated. The term "protein having peptidoglycan-degrading activity" (hereinafter, also referred to as "peptidoglycan-degrading enzyme") refers to a protein accelerating the above reaction.

Peptidoglycan is efficiently degraded through degradation of glycosidic linkages between saccharides forming a polysaccharide and peptide linkages within oligopeptides, etc. Sites that can be degraded by a peptidoglycan-degrading enzyme are indicated with arrows in FIG. 1. Examples of the protein having activity to degrade peptidoglycan include: (1) a protein having activity to degrade a glycosidic linkage between N-acetylglucosamine and N-acetylmuramic acid, (2) a protein having activity to degrade a glycosidic linkage between N-acetylmuramic acid and N-acetylglucosamine, (3) a protein having activity to degrade an amide linkage between N-acetylmuramic acid and L-alanine, and (4) a protein having activity to degrade each peptide linkage.

Specific examples of (1) include N-acetylglucosaminidase, specific examples of (2) include N-acetylmuramidase and lytic transglycosidase, specific examples of (3) include N-acetylmuramoyl-L-alanineamidase, and specific examples of (4) include L,D-endopepti dase, D,L-endopeptidase, carboxypeptidase, and D,D-endopeptidase.

Examples of a method for investigating if a protein is the protein having peptidoglycan-degrading activity include a method that involves reacting a target protein with peptidoglycan in a buffer solution for a certain time, and then measuring the degradation of the peptidoglycan. Examples of a method for investigating degradation include, but are not particularly limited to, a method for measuring the turbidity of peptidoglycan, a method for detecting peptidoglycan with the use of an SLP reagent, and a method for detecting a degradation product derived from peptidoglycan with the use of high-performance liquid chromatography (HPLC); mass spectrometry method (MS); thin-layer chromatography (TLC); nuclear magnetic resonance (NMR); gas chromatography (GC) or the like.

Examples of a method for investigating if a protein is the protein (2) having activity to degrade a glycosidic linkage between N-acetylmuramic acid and N-acetylglucosamine from among peptidoglycan-degrading activities include a method using *Micrococcus lysodeikticus* as a substrate. Specifically, a cultured cell of *Micrococcus lysodeikticus* may also be used as a substrate, or a Lysozyme activity kit (manufactured by Sigma-Aldrich), an EnzChek Lysozyme assay kit (manufactured by ThermoFisher Scientific) or the like may also be used.

Examples of a method for investigating (3) amidase activity to hydrolyze an amide linkage between N-acetylmuramic acid and L-alanine among peptidoglycan-degrading activities include the one as described in Appl Microbiol Biotechnol. 2015, October, 99(20):8563-73, such as a method using L-aniline-p-nitroanilide hydrochloride (manufactured by Sigma-Aldrich) as a substrate for N-acetylmuramoyl-L-alanineamidase.

[Protein Represented by SEQ ID NO: 2 or 4]

The protein according to an embodiment of the present invention is any one of the following proteins.

(A1) A protein comprising the amino acid sequence at positions 1 to 164 of SEQ ID NO: 2, and having peptidoglycan-degrading activity.

(B1) A protein comprising the amino acid sequence at positions 1 to 493 of SEQ ID NO: 4, and having peptidoglycan-degrading activity.

The amino acid sequence at positions 1 to 164 of SEQ ID NO: 2 and the amino acid sequence at positions 1 to 493 of SEQ ID NO: 4 are the amino acid sequences of mature protein bodies as predicted from the genomic sequence of NITE BP-02779. Whether or not a protein has peptidoglycan-degrading activity can be determined by the above methods, for example. Such a protein having peptidoglycan-degrading activity can degrade a target microorganism, so that the volume of excess sludge can be reduced.

The protein according to an embodiment of the present invention may be a variant of the protein having the amino acid sequence at positions 1 to 164 of SEQ ID NO: 2 or the amino acid sequence at positions 1 to 493 of SEQ ID NO: 4, as long as the peptidoglycan-degrading activity is maintained. Such a variant having peptidoglycan-degrading activity maintained therein may also be referred to as "conservative variant". In the present invention, examples of a protein that is specified as the protein having peptidoglycan-degrading activity include, in addition to the above proteins, conservative variants thereof, and a fusion protein formed of such a protein and another peptide.

Conservative variants of peptidoglycan-degrading enzymes are exemplified as follows.

The protein according to an embodiment of the present invention may be a protein having the amino acid sequence at positions 1 to 164 of SEQ ID NO: 2 or the amino acid sequence at positions 1 to 493 of SEQ ID NO: 4 with a substitution, deletion, insertion, or addition of one or several amino acid residues, as long as the peptidoglycan-degrading activity is maintained. "One or several" differs depending on the positions, types, and the like of amino acid residues in the conformation of a protein, and may refer to 1 to 10, 1 to 8, 1 to 5, or 1 to 3, for example.

The protein according to an embodiment of the present invention may be a protein having an amino acid sequence having high identity such as 90% or more, 93% or more, 95% or more, 97% or more, or 99% or more identity to the amino acid sequence at positions 1 to 164 of SEQ ID NO: 2 or the amino acid sequence at positions 1 to 493 of SEQ ID NO: 4, as long as the peptidoglycan-degrading activity is maintained.

The above amino acid residue mutations are conservative mutations by which protein functions are maintained normally. A typical conservative mutation is a conservative substitution. The conservative substitution is a mutation such that Phe, Trp and Tyr are substituted with each other when an aromatic amino acid is at the substitution site, a substitution such that Leu, Ile and Val are substituted with each other when a hydrophobic amino acid is at the substitution site, a substitution such that Gln and Asn are substituted with each other when a polar amino acid is at the substitution site, a substitution such that Lys, Arg and His are substituted with each other when a basic amino acid is at the substitution site, a substitution such that Asp and Glu are substituted with each other when an acidic amino acid is at the substitution site, and a substitution such that Ser and Thr are substituted with each other when an amino acid having a hydroxyl group is at the substitution site. Examples of such substitution that is considered as a conservative substitution include, specifically, a substitution of Ala with Ser or Thr, a substitution of Arg with Gln, His or Lys, a substitution of Asn with Glu, Gln, Lys, His or Asp, a substitution of Asp with Asn, Glu or Gln, a substitution of Cys with Ser or Ala, a substitution of Gln with Asn, Glu, Lys, His, Asp or Arg, a substitution of Glu with Gly, Asn, Gln, Lys or Asp, a substitution of Gly with Pro, a substitution of His with Asn, Lys, Gln, Arg or Tyr, a substitution of Ile with Leu, Met, Val or Phe, a substitution of Leu with Ile, Met, Val or Phe, a substitution of Lys with Asn, Glu, Gln, His or Arg, a substitution of Met with Ile, Leu, Val or Phe, a substitution of Phe with Trp, Tyr, Met, Ile or Leu, a substitution of Ser with Thr or Ala, a substitution of Thr with Ser or Ala, a substitution of Trp with Phe or Tyr, a substitution of Tyr with His, Phe or Trp, and a substitution of Val with Met, Ile or Leu. Examples of amino acid residue mutations include mutations generated by naturally occurring mutations (mutants or variants) based on individual differences among organisms from which proteins are derived, differences in species, etc.

The protein according to an embodiment of the present invention may be a fusion protein formed by fusion with another peptide. Examples of another peptide include a marker peptide (marker protein), a peptide tag, and pro-sequence or prepro-sequence, such as a secretory signal peptide. Only one type of peptide may be ligated to a peptidoglycan-degrading enzyme or 2 or more types of peptides may also be linked thereto. When a peptidoglycan-degrading enzyme is a fusion protein formed by fusion with a signal peptide, after expression thereof in host cells capable of performing secretion, the signal peptide is cleaved, and thus only the peptidoglycan-degrading enzyme portion (mature protein) can be secreted extracellularly. When the peptidoglycan-degrading enzyme is a fusion protein, the above identity refers to identity of the mature protein portion excluding the other peptide portion.

Examples of a marker peptide are not particularly limited, as long as it is a peptide capable of functioning as a marker, and include alkaline phosphatase, Fc regions of an antibody, HRP and GFP. Examples of a peptide tag include, but are not particularly limited to, conventionally known peptide tags such as a Myc tag, a His tag, a FLAG tag, and a GST tag. As a secretory signal peptide, in addition to a secretory signal peptide of the peptidoglycan-degrading enzyme itself of NITE BP-02779, a secretory signal peptide capable of functioning in a host in which the peptidoglycan-degrading enzyme is expressed can be used. A fusion protein can be prepared by a general method.

The protein according to an embodiment of the present invention may be any one of the following proteins (a1) to (a4):

(a1) a protein consisting of the amino acid sequence at positions 1 to 164 of SEQ ID NO: 2;

(a2) a protein consisting of the amino acid sequence at positions 1 to 164 of SEQ ID NO: 2 with a substitution of Ala at position 1 with Met;

(a3) a protein consisting of the amino acid sequence at positions 1 to 164 of SEQ ID NO: 2 with a substitution of Ala at position 1 with Met and addition of the amino acid sequence represented by MetGlySerSerHisHisHisHisHisHisSerSerGlyLeuValProArgGlySerHis (SEQ ID NO: 21) to the N-terminus of the Met; and (a4) a protein consisting of the amino acid sequence at positions 1 to 164 of SEQ ID NO: 2 with addition of Met to the N-terminus of Ala at position 1.

The protein according to an embodiment of the present invention may be any one of the following proteins (b1) to (b4):

(b1) a protein consisting of the amino acid sequence at positions 1 to 493 of SEQ ID NO: 4;

(b2) a protein consisting of the amino acid sequence at positions 1 to 493 of SEQ ID NO: 4 with a substitution of Glu at position 1 with Met;

(b3) a protein consisting of the amino acid sequence at positions 1 to 493 of SEQ ID NO: 4 with a substitution of Glu at position 1 with Met and addition of the amino acid sequence represented by SEQ ID NO: 21 to the N-terminus of the Met; and (b4) a protein consisting of an amino acid sequence at positions 1 to 493 of SEQ ID NO: 4 with addition of Met to the N-terminus of Glu at position 1.

The protein consisting of the amino acid sequence at positions 1 to 164 of SEQ ID NO: 2 is considered to have activity (2) to degrade a glycosidic linkage between N-acetylmuramic acid and N-acetylglucosamine among the above peptidoglycan-degrading activities. (A1) The protein comprising the amino acid sequence at positions 1 to 164 of SEQ ID NO: 2 and having peptidoglycan-degrading activity, (A2) the protein comprising the amino acid sequence at positions 1 to 164 of SEQ ID NO: 2 with a substitution, deletion, insertion or addition of 1 to 10 amino acid residues, and having peptidoglycan-degrading activity, and (A3) the protein comprising an amino acid sequence having 90% or more identity to the amino acid sequence at positions 1 to 164 of SEQ ID NO: 2, and having peptidoglycan-degrading activity preferably have activity (2) to degrade a glycosidic linkage between N-acetylmuramic acid and N-acetylglucosamine among the above peptidoglycan-degrading activities.

The protein consisting of the amino acid sequence at positions 1 to 493 of SEQ ID NO: 4 is considered to have (3) N-acetylmuramoyl-L-alanine amidase activity among the above peptidoglycan-degrading activities. (B1) The protein comprising the amino acid sequence at positions 1 to 493 of SEQ ID NO: 4 and having peptidoglycan-degrading activity, (B2) the protein comprising the amino acid sequence at positions 1 to 493 of SEQ ID NO: 4 with a substitution, deletion, insertion or addition of 1 to 10 amino acid residues and having peptidoglycan-degrading activity, and (B3) the protein comprising an amino acid sequence having 90% or more identity to the amino acid sequence at positions 1 to 493 of SEQ ID NO: 4, and having peptidoglycan-degrading activity preferably have (3) N-acetylmuramoyl-L-alanine amidase activity among the above peptidoglycan-degrading activities.

The proteins according to (A1) to (A3) and (B1) to (B3) may be synthesized proteins, and may be purified or isolated proteins. The proteins according to (A1) to (A3) and (B1) to (B3) may be proteins derived from NITE BP-02779, and may be synthesized or generated artificially or within the cells of NITE BP-02779 or another organism.

[DNA Encoding Peptidoglycan-Degrading Enzyme]

The DNA according to the present invention is a DNA encoding the above protein. Specific examples of the DNA include a DNA encoding the amino acid sequence at positions 1 to 164 of SEQ ID NO: 2, a DNA encoding the amino acid sequence at positions 1 to 493 of SEQ ID NO: 4, and DNAs encoding conservative variants of proteins having these amino acid sequences. The DNA according to an embodiment of the present invention may be a DNA having the nucleotide sequence at positions 205 to 696 of SEQ ID NO: 1 or the nucleotide sequence at positions 85 to 1563 of SEQ ID NO: 3. SEQ ID NO: 1 and SEQ ID NO: 3 are nucleotide sequences based on the genomic sequence of NITE BP-02779 and encode mature protein bodies having peptidoglycan-degrading activity. The DNA according to the present invention may also contain a nucleotide sequence encoding an initiation codon and/or another peptide on the 5' end side of the above nucleotide sequence, and may contain a stop codon at the 3' end of the above nucleotide sequence. The DNA may also be a recombinant DNA. The DNA may be a synthesized DNA or a complementary DNA (cDNA). The DNA may be a purified or an isolated DNA.

The DNA according to the present invention is not limited to a DNA consisting of a sequence of NITE BP-02779 and may also be a DNA comprising a nucleotide sequence in which codons encoding amino acids in its coding region are substituted with other equivalent codons encoding the same amino acids. The DNA according to an embodiment of the present invention may also be a DNA comprising a nucleotide sequence in which codon expression frequency (codon usage) is altered to improve the expression of a protein having peptidoglycan-degrading activity.

Examples of the DNA according to an embodiment of the present invention include a DNA hybridizable under stringent conditions to a probe having a nucleotide sequence complementary to the above nucleotide sequence, or a probe that can be prepared from the above complementary nucleotide sequence, and encoding a protein having peptidoglycan-degrading activity. Stringent conditions refers to conditions where namely a specific hybrid is formed but any non-specific hybrid is not formed. Examples of such conditions can include conditions where DNAs having high identity to each other, such as DNAs having 50% or more, 65% or more, 80% or more, preferably 90% or more, more preferably 95% or more, further preferably 97% or more, and particularly preferably 99% or more identity to each other hybridize to each other, but DNAs having identity lower than such percentage to each other do not hybridize to each other, or washing conditions for general southern hybridization, specifically, conditions where washing is performed once, preferably 2 to 3 times at salt concentrations and temperatures corresponding to 60° C., 1×SSC and 0.1% SDS, preferably 60° C., 0.1×SSC and 0.1% SDS, more preferably 68° C., 0.1×SSC and 0.1% SDS. Further, when a DNA fragment having a length of about 300 bp is used as a probe, for example, examples of washing conditions for hybridization include 50° C., 2×SSC and 0.1% SDS.

The percentage of identity between two sequences can be determined using a mathematical algorithm, for example. Examples of the mathematical algorithm include an algorithm described in Myers and Miller (1988) CABIOS, 4: 11-17, a local homology algorithm described in Smith et al (1981) Adv. Appl. Math. 2: 482, a homology alignment algorithm described in Needleman and Wunsch (1970) J. Mol. Biol. 48: 443453, a method of searching for similarity described in Pearson and Lipman (1988) Proc. Natl. Acad. Sci. 85: 2444-2448, and an improved algorithm of Karlin and Altschul (1990) Proc. Natl. Acad. Sci. USA, 872264 described in Karlin and Altschul (1993) Proc. Natl. Acad. Sci. USA, 90: 587-5877.

With the use of programs based on these mathematical algorithms, sequence comparison (alignment) for determining sequence identity can be performed. Such a program can be adequately executed by a computer. Examples of such a program include, but are not particularly limited to, PC/Gene program, CLUSTAL (available from Intelligenetics, Mountain View, Calif.), as well as ALIGN program (Version 2.0), Wisconsin Genetics Software Package, Version 8 (available from Genetics Computer Group (GCG), 575 Science Drive, Madison, Wis., USA) such as GAP, BESTFIT, BLAST, FASTA and TFASTA. Alignment to be performed using these programs can be performed using initial parameters, for example. The CLUSTAL program is described well in HigGlns et al. (1988) Gene 73: 237-244, HigGlns et al. (1989) CABIOS 5: 151-153, Corpet et al. (1988) Nucleic Acids Res. 16: 1088190, Huang et al. (1992) CABIOS 8: 155-65 and Pearson et al. (1994) Meth. Mol. Biol. 24: 307-331.

In order to obtain a nucleotide sequence having identity to a nucleotide sequence encoding a target protein, for example, a BLAST nucleotide search can be performed using the BLASTN program, score=100, word length=12. In order to obtain an amino acid sequence having identity to a target protein, for example, a BLAST protein search can be performed using the BLASTX program, score=50, word length=3. For the BLAST nucleotide search and the BLAST protein search, refer to http://www.ncbi.nlm.nih.gov. In order to obtain a gapped alignment for comparison, Gapped BLAST (BLAST 2.0) can be used. PSI-BLAST (BLAST 2.0) can be used to perform repeated searches for detection of the distant relationship between sequences. Regarding Gapped BLAST and PSI-BLAST, refer to Altschul et al. (1997) Nucleic Acids Res. 25: 3389. When BLAST, Gapped BLAST, or PSI-BLAST is used, the initial parameters of each program (for example, BLASTN for a nucleotide sequence, BLASTX for an amino acid sequence) can be used. Alignment may also be performed manually.

Identity between two sequences is calculated as the percentage of residues matching between two sequences when the two sequences are aligned in such a manner that the two sequences match each other to the maximum extent.

The DNA according to the present invention can be obtained by chemical synthesis, or, from NITE BP-02779 by PCR or the like.

[Vector]

The vector according to the present invention contains the above DNA. A vector is a nucleic acid molecule capable of amplifying and maintaining DNA, and can be an expression vector or a cloning vector. The vector according to the present invention may be constructed by incorporating the above DNA into a basic vector according to a general genetic engineering technique. A basic vector can be independently replicated in host cells, for example, can be isolated and purified from host cells, and has a detectable marker. The DNA according to the present invention is inserted into an expression vector that can be used in host cells to be subjected to gene transfer. The vector is introduced into host cells, so that the protein having peptidoglycan-degrading activity can be expressed in the host cells.

The basic vector may be a vector derived from a bacterial plasmid, a vector derived from a yeast plasmid, a viral vector, a cosmid vector, a phagemid vector, or an artificial chromosome vector, for example. Examples of such a basic vector include pBR322, a pUC plasmid vector, and a pET-based plasmid vector. Specifically, when *Escherichia coli* is used as a host cell, examples thereof can include vectors pUC19, pUC18, and pUC119 (manufactured by Takara Shuzo Co., Ltd.), phagemid pBluescriptII (manufactured by Stratagene), pET28a(+) vector and pET22b(+) vector (manufactured by Merck Millipore). When a budding yeast is used as a host cell, examples thereof can include vectors pGBT9, pGAD424, and pACT2 (manufactured by Clontech). When mammalian cells are used as host cells, examples thereof can include vectors such as pRc/RSV and pRc/CMV (Invitrogen), bovine papilloma virus vector pBPV (manufactured by Amersham Pharmacia Biotech, Inc.), EB virus vector pCEP4 (manufactured by Invitrogen), a vaccinia virus vector, a retrovirus vector, a lentivirus vector, an adenovirus vector, and an adeno-associated virus vector. When insect cells are used as host cells, examples thereof can include a baculovirus vector.

When the vector according to the present invention is constructed using a basic vector having an autonomous replication origin (ori), the vector is retained within cells as an episome when the vector is introduced into host cells. If a vector, in which SV40 ori has been incorporated, is introduced into COS cells or the like transformed with an ori-deficient SV40 genome, the number of copies of the vector in the cells can be significantly increased, for example.

The expression vector may have a promoter sequence and a terminator sequence for expression of an incorporated gene. The promoter is not particularly limited as long as it functions in host cells. "Promoter that functions in a host" refers to a promoter having promoter activity in a host and being capable of controlling the expression of an incorporated gene. In general, a DNA sequence to be incorporated into a basic vector is inserted downstream of a promoter in a state where the promoter can function. For example, a basic vector is provided with a cloning site located downstream of the promoter sequence. The basic vector may also have a selection marker sequence.

The promoter may be a promoter derived from a host or a heterologously derived promoter. The promoter may be an inherent promoter of a peptidoglycan-degrading enzyme gene or a promoter of another gene. When host cells are *Escherichia coli* cells, examples of the promoter can include an *Escherichia coli* lactose operon promoter (lacP), a tryptophan operon promoter (trpP), an arginine operon promoter (argP), a galactose operon promoter (galP), a tac promoter, a T7 promoter, a T3 promoter, and X phage promoters (λ-pL, λ-pR). When host cells are animal cells or fission yeast, examples of the promoter can include a Rous sarcoma virus (RSV) promoter, a cytomegalovirus (CMV) promoter, a simian virus (SV40) early or late promoter, and a mouse papilloma virus (MMTV) promoter. When host cells are budding yeast, examples of the promoter can include an ADH1 promoter. The ADH1 promoter can be prepared by a general genetic engineering method using a yeast expression vector pAAH5 [available from Washington Research Foundation, Ammerer et al., Method in Enzymology, 10 1 part (p. 192-201)] retaining the ADH1 promoter and ADH1 terminator. Vector pACT2 having the ADH1 promoter makes it possible to express a gene of interest in a large amount in a budding yeast such as CG1945 (manufactured by Clontech), when the gene of interest is inserted downstream of the ADH1 promoter.

[Transformant]

The transformant according to the present invention contains the above DNA according to the present invention or the above vector according to the present invention. The transformant containing the DNA according to the present invention or the vector according to the present invention can cause the expression of a protein having peptidoglycan-degrading activity.

As host cells into which the DNA according to the present invention or the vector according to the present invention is introduced, eucaryotic cells or prokaryotic cells can be used, for example. Examples thereof include bacteria, fungi, plant cells, animal cells, and insect cells. Host cells are preferably *Escherichia coli* cells. Through introduction of DNA or a vector into host cells, host cells are transformed, and thus a transformant can be prepared.

The DNA according to the present invention or the vector according to the present invention may be retained outside the chromosome within host cells, or incorporated into the chromosome. In such a transformant, the DNA according to the present invention or the vector according to the present invention is preferably retained in a state where a gene can be expressed under the control of a promoter that functions within host cells.

As a method for introducing the DNA according to the present invention or the vector according to the present invention into a host cell, a general introduction method may be applied according to a host cell. When *Escherichia coli* is used as a host cell, examples thereof can include gene transfer methods such as a calcium chloride method and an electroporation method described in J. Sambrook, E. F. Frisch, T. Maniatis "Molecular Cloning $2^{nd}$ edition)", issued by Cold Spring Harbr Laboratory (1989). When mammalian cells or insect cells are used as host cells, examples thereof can include gene transfer methods such as a calcium phosphate method, a DEAE dextran method, an electroporation method, and a lipofection method. When a yeast is used as a host cell, examples thereof can include gene transfer methods such as a lithium method that is used for a Yeast transformation kit (Clontech). When a virus is used as a vector, a viral genome in which the DNA according to the present invention has been inserted by the above gene transfer method can be introduced into a host cell, and through infection of a host cell with a viral particle containing the viral genome, the DNA according to the present invention can be introduced into the host cell.

A selection marker may be used to select a transformant into which the DNA according to the present invention or the vector according to the present invention has been introduced. For example, the DNA or the vector according to the present invention and a selection marker gene are introduced simultaneously into host cells, and then the cells are cultured by a method according to the properties of the selection marker. For example, when a selection marker gene is a gene that imparts drug resistance to a selection drug exhibiting lethal activity on host cells, host cells into which the DNA or the vector according to the present invention has been introduced may be cultured using a medium supplemented with the selection drug. Examples of a combination of a gene that imparts drug resistance and a selection drug can include a combination of a gene imparting neomycin resistance and neomycin, a combination of a gene imparting hygromycin resistance and hygromycin, and a combination of a gene imparting blasticidinS resistance and blasticidinS. Further, when a marker gene is a gene complementing the auxotrophy of host cells, the host cells in which the DNA or the vector according to the present invention has been introduced may be cultured using a minimal medium not containing a nutrient corresponding to the auxotrophy. The transformant can also be selected based on the activity of an enzyme to be expressed by the use of the DNA or the vector according to the present invention.

In order to obtain a transformant in which the DNA according to the present invention is located within the chromosome of a host cell, for example, first the vector according to the present invention and a vector having a marker gene are linearized by digestion with a restriction enzyme or the like, and then introduced into host cells by the above gene transfer method. After the introduced cells are cultured for generally several weeks, a transformant of interest may be obtained based on the expression level of the marker gene. When a gene that imparts resistance to a selection drug is used as a marker gene, the vector according to the present invention and a vector having the marker gene are introduced into host cells by the above gene transfer method, cells are subcultured in a medium supplemented with the selection drug for several weeks or longer, and then a selection-drug-resistant clone that has survived in the form of colonies is pure-cultured, so that a transformant in which the DNA according to the present invention has been introduced into the chromosomes of the host cells can be obtained. The incorporation of the DNA according to the present invention into the chromosomes of host cells may be confirmed by preparing the genomic DNA of cells according to a general genetic engineering method, performing PCR, southern hybridization or the like using DNA having a partial nucleotide sequence of the introduced DNA according to the present invention as a primer or a probe, and then detecting the presence of the DNA according to the present invention. Such a transformant in which the DNA according to the present invention has been introduced into the chromosomes of host cells can be cryopreserved and then can be thawed as necessary for use. This can save the time and labor required for preparation of a transformant in every experiment, and makes it possible to conduct a test using a transformant the properties and handling conditions of which have been confirmed in advance.

[Production of Protein According to the Present Invention]

The protein according to the present invention can be obtained from NITE BP-02779, for example. The expression "obtained from NITE BP-02779" means to obtain the protein from within cells of or a culture supernatant of NITE-BP02779. For example, when the protein according to the present invention is obtained from within cells, the protein according to the present invention can be collected by appropriately disrupting, lysing cells or extracting etc., from cells. Cells can be collected from a culture by centrifugation or the like. Cell disruption, and lysis or extraction etc., can be performed by a known method. Examples of such a method include ultrasonic disintegration, disruption using dyno-mill, bead disruption, French press disruption, and lysozyme treatment. One type of these methods may be used alone or two or more types thereof may be adequately used in combination. When the protein according to the present invention is accumulated in a culture supernatant, the culture supernatant is obtained by centrifugation or the like and then the protein according to the present invention can be collected from the culture supernatant.

The protein according to the present invention can be purified by a known method that is employed for enzyme purification. Examples of such a method include sulfur fractionation, ion exchange chromatography, hydrophobic chromatography, affinity chromatography, gel filtration chromatography, and isoelectric point precipitation. One type of these methods may be used alone, or two or more types thereof may be used in combination as appropriate. Purification of the protein according to the present invention can be performed to a desired degree.

The protein according to the present invention can also be produced using a transformant prepared by introducing DNA encoding the protein into an appropriate host. DNA is preferably incorporated into a vector and then used for transformation. The protein according to the present invention may be artificially synthesized in a cell-free system.

When the protein according to the present invention is produced using a transformant, the transformant may be cultured by a method for culturing host cells. When the transformant is a microorganism, it can be cultured using various media appropriately containing a carbon source, a nitrogen source, an organic or inorganic salt, etc., which are usually used for culturing microorganisms, for example.

Examples of the carbon source include: sugars such as glucose, dextrin and sucrose; sugar alcohols such as glycerol; organic acids such as fumaric acid, citric acid and pyruvic acid; and animal oils, vegetable oils and molasses. The amount of such a carbon source to be added to a medium is usually about 0.1 to 30% (w/v) with respect to the culture solution.

Examples of the nitrogen source include: natural organic nitrogen sources such as meat extract, peptone, yeast extract, malt extract, soybean flour, Corn Steep Liquor, cottonseed powder, dried yeast, and casamino acid; amino acids; salts of inorganic acids such as sodium nitrate, ammonium salts of inorganic acids such as ammonium chloride, ammonium sulfate and ammonium phosphate; ammonium salts of organic acids such as ammonium fumarate and ammonium citrate and urea. Of these, ammonium salts of organic acids, natural organic nitrogen sources, amino acids and the like can also be used as carbon sources in many cases. The amount of such a nitrogen source to be added to a medium is usually about 0.1 to 30% (w/v) with respect to the culture solution.

Examples of the organic salt or inorganic salt can include chlorides such as potassium, sodium, magnesium, iron, manganese, cobalt and zinc, sulfates, acetates, carbonates and phosphates. Specific examples thereof include sodium chloride, potassium chloride, magnesium sulfate, ferrous sulfate, manganese sulfate, cobalt chloride, zinc sulfate, copper sulfate, sodium acetate, calcium carbonate, monopotassium hydrogen phosphate and dipotassium hydrogen phosphate. The amount of such an organic salt and/or inorganic salt to be added to the medium is usually about 0.0001 to 5% (w/v) with respect to the culture solution.

In the case of a transformant in which a gene is expressed in a form such that an allolactose-induced promoter such as a tac promoter, a trc promoter, or a lac promoter is connected to the DNA according to the present invention, isopropyl-thio-β-D-galactoside (IPTG) can be added in a small amount as an inducer to a medium for production of the protein according to the present invention, for example.

The transformant according to the present invention may be cultured according to a method that is generally employed for culturing host cells. Examples of such a method include liquid culture and solid culture, such as in vitro shaking culture, reciprocating shaking culture, Jar Fermenter culture, and tank culture. The culture temperature can be appropriately varied within the range in which the transformant can grow, but ranges from usually about 15° C. to about 40° C. The pH of the medium ranges from preferably about 6.0 to about 8.0. The culturing time varies depending on the culturing conditions, but may be about 1 day to about 5 days.

Through culturing of the transformant according to the present invention, a culture containing the protein according to the present invention can be obtained. The protein according to the present invention can be accumulated in the cells of and/or culture supernatant of the transformant, for example. That the protein according to the present invention is produced can be confirmed by measuring peptidoglycan-degrading activity of appropriate fractions such as a culture supernatant and an intracellular extract according to the above method.

The protein according to the present invention may be obtained by disrupting, lysing, extracting and purifying a transformant as appropriate according to the same method as that for the above NITE BP-02779. The protein according to the present invention is not limited to the purified protein according to the present invention, and an arbitrary fraction containing the protein according to the present invention may be used as "the protein according to the present invention" for applications such as degradation of peptidoglycan. The fraction containing the protein according to the present invention is not particularly limited, as long as the protein according to the present invention is contained in such a manner that it can act on peptidoglycan. Examples of such fraction include transformants, culture supernatants of transformants, crushed products, lysates, extracts (cell-free extracts), etc., partially purified products thereof (crude purified products), and combinations thereof. All of these fractions may be used alone for applications such as degradation of peptidoglycan, or may be used together with the purified protein according to the present invention. In addition to the protein according to the present invention, other enzymes different from the protein according to the present invention can be generated and accumulated in the culture. The protein according to the present invention may be collected as a mixture with such other enzymes, or may be collected separately from such other enzymes.

[Microorganism Degrading Preparation]

The microorganism degrading preparation comprises at least one selected from the group consisting of the protein according to the present invention, and the transformant according to the present invention and a culture thereof. The culture of the transformant includes the cultured transformant, the culture supernatant of the transformant, the disrupted product, the lysate, the cell extract (cell-free extract), etc., and a partially purified product thereof (crudely purified products), and combinations thereof.

The microorganism degrading preparation contains preferably a protein consisting of the amino acid sequence at positions 1 to 164 of SEQ ID NO: 2 and/or a protein consisting of the amino acid sequence at positions 1 to 493 of SEQ ID NO: 4. The microorganism degrading preparation may contain one type of enzyme having peptidoglycan-degrading activity or 2 or more types thereof in combination. The microorganism degrading preparation may contain an ingredient other than these as long as peptidoglycan-degrading activity is not inhibited. The microorganism degrading preparation can contain one type of or two or more types of transformant.

The contents of the protein according to the present invention, and the transformant according to the present invention and a culture thereof in the microorganism degrading preparation are not particularly limited and may be set as appropriate according to the type and concentration of a target microorganism, and the usage environment of the microorganism degrading preparation (volume of reaction system, temperature, etc.).

The microorganism degrading preparation contains a protein having peptidoglycan-degrading activity or a transformant that can express the protein having peptidoglycan-degrading activity, so as to be able to degrade peptidoglycan. The microorganism degrading preparation can degrade a target microorganism having peptidoglycan. The target microorganism is a bacterium that composes preferably excess sludge. The target microorganism may be a dead bacterium or a living bacterium. The microorganism degrading preparation can contribute to the volume reduction of excess sludge.

Whether or not a microorganism is degraded can be confirmed by a method usually employed by those skilled in the art. Examples of such a confirmation method include a method of detecting the degradation of a target microorganism in a medium or a buffer solution after the reaction of a microorganism degrading preparation with the target microorganism in an appropriate medium or a buffer solution for a certain time. Examples of the method for detecting the degradation of a target microorganism include, but are not particularly limited to, a method for measuring the turbidity of a target microorganism, a method for detecting a target microorganism with an SLP reagent, a method for detecting the DNA of a target microorganism by PCR, and a method for measuring the dry cell weight of a target microorganism, and a method for detecting a degraded product derived from a target microorganism using a high performance liquid chromatography (HPLC); mass spectrometry (MS); thin layer chromatography (TLC); nuclear magnetic resonance (NMR); gas chromatography (GC), etc. It is also possible to investigate whether a target microorganism is degraded by the above method for investigating the peptidoglycan degrading activity.

When the degradation of a target microorganism is investigated in terms of turbidity, the expression "a target microorganism is degraded" means that the turbidity after the reaction is significantly lower than the turbidity before the reaction, for example, the turbidity after the reaction is 80% or less, preferably 50% or less, and more preferably 30% or less of the turbidity before the reaction. When the degradation of a target microorganism is investigated in terms of the dry cell weight, the expression that "target microorganism is degraded" means that, for example, the dry cell weight after the reaction is significantly lower than that before the reaction, for example, the dry cell weight after the reaction is 95% or less, and preferably 90% or less of that before the reaction.

The dosage form of the microorganism degrading preparation is not particularly limited, as long as the functions of the protein according to the present invention, and the transformant according to the present invention and a culture thereof are not lost. Examples of the dosage form include liquids, suspensions, powders, solids, capsule inclusions, or frozen or lyophilized products thereof. Upon formulation, for example, additives such as excipients, binders, disintegrants, lubricants, stabilizers, diluents and surfactants can be used.

The microorganism degrading preparation can be used by putting it into a sludge treatment device, a wastewater treatment device, etc. in which excess sludge is generated. The microorganism degrading preparation can also be used by putting it in a tank or the like in which excess sludge or target microorganisms are accumulated.

One embodiment of the present invention is, in production of the microorganism degrading preparation, the use of at least one selected from the group consisting of the protein according to the present invention, and the transformant according to the present invention and a culture thereof.

[Method for Degrading Microorganism]

The method for degrading microorganisms comprises allowing at least one selected from the group consisting of the protein according to the present invention, and the transformant according to the present invention and a culture thereof to act on a target microorganism. Examples of the culture of a transformant include a cultured transformant, the culture supernatant of a transformant, disrupted products, lysates, cell extracts (cell-free extract) etc., partially purified products thereof (crudely purified products), and combinations thereof. The step of allowing at least one selected from the group consisting of the protein according to the present invention, and the transformant according to the present invention and a culture thereof to act on a target microorganism may also be performed using the above microorganism degrading preparation.

The expression "allowing the protein according to the present invention to act on a target microorganism" means that the protein according to the present invention is brought into contact with a target microorganism, for example. The expression "allowing the transformant according to the present invention to act on a target microorganism" means that the transformant according to the present invention is cultured in the presence of a target microorganism, for example. The expression "allowing the culture of the transformant according to the present invention to act on a target microorganism" means that the culture of the transformant, preferably a protein having peptidoglycan-degrading activity contained in the culture is brought into contact with a target microorganism, for example.

According to the method for degrading microorganisms according to the present invention, a target microorganism having peptidoglycan can be degraded. Such a target microorganism is preferably a bacterium composing excess sludge. The target microorganism may be a dead bacterium or a living bacterium. According to the method for degrading microorganisms, it is possible to contribute to the volume reduction of excess sludge.

The method for degrading microorganisms comprises allowing preferably the protein consisting of the amino acid sequence at positions 1 to 164 of SEQ ID NO: 2 and/or the protein consisting of the amino acid sequence at positions 1 to 493 of SEQ ID NO: 4 to act on a target microorganism. In this step, one type of the protein having peptidoglycan-degrading activity may be used and 2 or more types thereof may be used in combination. In the method for degrading microorganisms, one type of or two or more types of transformant may be allowed to act on a target microorganism.

The step of allowing the protein according to the present invention, and the transformant according to the present invention and a culture thereof to act on a target microorganism is not particularly limited, as long as the step is performed under conditions where the protein according to the present invention is not lost or the peptidoglycan-degrading activity of the protein according to the present invention is not lost, or conditions where no transformant is killed and the protein can be synthesized. This step may be performed under conditions of temperatures ranging from 20° C. to 35° C. or temperatures ranging from 25° C. to 30° C., for example, and under conditions of the pH ranging from 5.5 to 8.0 or the pH ranging from 6.0 to 7.5.

The amount of the protein according to the present invention, and the transformant according to the present invention and a culture thereof, which is used in the method for degrading microorganisms, can be set as appropriate in view of the type and concentration of a target microorganism, the volume of a reaction system, reaction temperature, etc.

Whether or not a target microorganism is degraded can be confirmed by a method described in the column of the microorganism degrading preparation.

One embodiment of the present invention is the use of at least one selected from the group consisting of the protein according to the present invention, and the transformant according to the present invention and a culture thereof, which are used for degrading a target microorganism. One embodiment of the present invention is the use of a microorganism degrading preparation containing at least one selected from the group consisting of the protein according to the present invention, and the transformant according to the present invention and a culture thereof, which are used for degrading a target microorganism.

EXAMPLES

Hereinafter, the present invention will be described in more detail with reference to examples, but the present invention is not limited to these examples.

Experiment 1. Isolation of Microorganism-Degrading Bacterium (Method)

Using medium containing the bacteria of the genus *Micrococcus* as a carbon source, a microorganism flora present in an environment (water) was cultured to subject the microorganisms that degrade the bacteria of the genus *Micrococcus* to enrichment culture. Then, several strains that had grown well were isolated from the enriched microorganism flora.

(Results)

Each of the isolated strains was investigated in terms of the ability to degrade the bacteria of the genus *Micrococcus*, and one strain demonstrated the ability to degrade the bacteria of the genus *Micrococcus*. Hereinafter, the strain that demonstrated the ability to degrade the bacteria of the genus *Micrococcus* may be referred to as "strain A".

Experiment 2. Identification of Strain A (Materials)

Forward primer for cloning (27F: SEQ ID NO: 5)

Reverse primer for cloning (1492R: SEQ ID NO: 6)

Primers for sequence analysis (339F: SEQ ID NO: 7, 536R: SEQ ID NO: 8, 907F: SEQ ID NO: 9)

(Method)

Strain A was identified by 16S rRNA genetic analysis, morphological observation and physiological and biochemical property tests.

16S rRNA genetic analysis was carried out by the following procedures. Genomic DNA was extracted from strain A, and then the 16S rRNA gene was amplified by PCR using the thus obtained genomic DNA as a template, the forward primer for cloning (27F) and the reverse primer for cloning (1492R). PCR amplification was carried out using KOD FX (manufactured by TOYOBO CO., LTD.), thereby purifying the PCR amplified product.

A cycle sequence reaction was carried out using the purified PCR amplified product. The cycle sequence reaction was carried out using a BigDye Terminator v3.1 Cycle Sequencing Kit. The thus obtained reaction solution was purified, and then the purified solution was subjected to the DNA sequence analysis (3730×1 DNA Analyzer) to determine the nucleotide sequence of 16S rRNA gene of the template DNA extracted from strain A.

Morphological observation and physiological and biochemical property tests were carried out by morphological observation using an optical microscope, and the method of BARROW et al. (Cowan and Steel's Manual for the Identification of Medical Bacteria 3rd Edition 1993, Cambridge University Press.) and API50CHB (manufactured by bioMerieux, Lyon, France).

(Results)

The nucleotide sequence (SEQ ID NO: 10) of the obtained 16S rRNA gene was subjected to homology analysis with the International Nucleotide Sequence Databases (DDBJ/ENA(EMBL)/GenBank). This sequence had 98.1% identity to the nucleotide sequence of 16S rRNA gene of *Tumebacillus permanentifrigoris* Eurl_9.5 among the type strains. However, a microorganism having the 16S rRNA gene completely identical to the obtained nucleotide sequence was not present. Further, strain A did not grow at 10° C., but *Tumebacillus permanentifrigoris* Eurl_9.5 having the highest identity to the 16S rRNA gene was not observed to have such property. For this reason, it was suggested that strain A is a new species different from the conventional *Tumebacillus*. Strain A was internationally deposited under *Tumebacillus* sp. NITE BP-02779.

The results of morphological observation and physiological and biochemical property tests on NITE BP-02779 are shown in Table 1 to Table 4.

TABLE 1

| Test items | | Results |
|---|---|---|
| Culture temperature (° C.) | | 25 |
| Cell morphology | | Rod-shaped (0.8-0.9 × 3.0-5.0 μm) |
| Gram staining | | + |
| Presence or absence of spore | | + |
| Motility | | – |
| Colony morphology | | Medium: R2A agar<br>Culture time: 48 hr<br>Diameter: 1-2 mm<br>Color tone: yellow<br>Shape: circular<br>Elevation condition: similar to a lens (elevated in the center)<br>Margin: undulate<br>Surface appearance etc.: smooth<br>Transparency: opaque<br>Viscosity: similar to butter |
| Growth temperature test (° C.) | 37 | + |
| | 45 | – |
| Catalase reaction | | +w |
| Oxidase reaction | | – |
| Acid/gas production from glucose (Acid production/gas production) | | –/– |
| O/f test (Oxidation/fermentation) | | –/– |

+: positive,
–: negative,
+w: weak reaction

TABLE 2

| Substrate ingredient (Fermentability test) | Test results | Substrate ingredient (Fermentability test) | Test results | Substrate ingredient (Fermentability test) | Test results |
|---|---|---|---|---|---|
| Control | – | α-Methyl-D-glucoside | – | D-Tagatose | – |
| Glycerol | – | N-Acetylglucosamine | – | D-Fucose | – |
| Erythritol | – | Amygdalin | – | L-Fucose | – |
| D-Arabinose | – | Arbutin | – | D-Arabitol | – |
| L-Arabinose | – | Aesculin | – | L-Arabitol | – |
| Ribose | – | Salicin | – | Gluconate | – |
| D-Xylose | – | Cellobiose | – | 2-Ketogluconate | – |
| L-Xylose | – | Maltose | – | 5-Ketogluconate | – |
| Adonitol | – | Lactose | – | | |
| β-Methyl-D-xylose | – | Melibiose | – | | |
| Galactose | – | Saccharose | – | | |
| Glucose | – | Trehalose | – | | |
| Fructose | – | Inulin | – | | |
| Mannose | – | Melezitose | – | | |
| Sorbose | – | Raffinose | – | | |
| Rhamnose | – | Starch | – | | |
| Dulcitol | – | Glycogen | – | | |
| Inositol | – | Xylitol | – | | |
| Mannitol | – | Gentiobiose | – | | |
| Sorbitol | – | D-Turanose | – | | |
| α-Methyl-D-mannoside | – | D-Lyxose | – | | |

+: positive,
–: negative

TABLE 3

| Substrate ingredients (Biochemistry test) | Test results |
|---|---|
| β-Galactosidase | – |
| Arginine dihydrolase | – |
| Lysine decarboxylase | – |
| Ornithine decarboxylase | – |

TABLE 3-continued

| Substrate ingredients (Biochemistry test) | Test results |
|---|---|
| Citric acid usability | – |
| $H_2S$ production | – |
| Urease | – |
| Tryptophan deaminase | – |
| Indole production | – |
| Acetoin production (VP) | – |
| Gelatinase | – |
| Nitrate reduction | – |

+: positive,
–: negative

TABLE 4

| Test items | Test results |
|---|---|
| Growth at 10° C. | – |
| Growth at pH 9.0 | + |
| Hydrolysis of starch | + |

+: positive,
–: negative

Experiment 3. Degradation Ability Evaluation of NITE BP-02779 on Excess Sludge (Killed Bacteria)-1

(Materials)

R2A Medium: Medium obtained by dissolving R2A Broth, DAIGO (manufactured by Nihon Pharmaceutical Co., Ltd.) in a proportion of 3.2 g relative to 1000 mL of ultrapure water, then being autoclaved Excess sludge (killed bacteria)-containing inorganic medium: Medium obtained by mixing 986 mL of a substrate solution, 3.0 mL of a solution A, 3.0 mL of a solution B, 3.0 mL of a solution C, 3.0 mL of a solution D and 1.8 mL of 1% phosphoric acid The substrate solution and solutions A to D used were as follows.

Substrate solution: Solution obtained by washing the excess sludge, then mixing the excess sludge with 986 mL of ultrapure water in such a way as to have a turbidity (OD660) of 0.2, and being autoclaved.

Solution A: Solution obtained by dissolving 4.35 g of dipotassium hydrogen phosphate, 1.70 g of monopotassium dihydrogen phosphate, 8.92 g of di-sodium hydrogen phosphate 12-Water and 0.34 g of ammonium chloride in ultrapure water, then being prepared to be 200 mL and autoclaved.

Solution B: Solution obtained by dissolving 4.50 g of magnesium sulfate heptahydrate in ultrapure water, then being prepared to be 200 mL and autoclaved.

Solution C: Solution obtained by dissolving 5.50 g of anhydrous calcium chloride in ultrapure water, then being prepared to be 200 mL and autoclaved.

Solution D: Solution obtained by dissolving 0.05 g of iron chloride hexahydrate in ultrapure water, then being prepared to be 200 mL and filter sterilized with a 0.2 μm syringe filter.

(Method)

NITE BP-02779 was seeded in R2A medium and cultured at 25° C. for 24 hours to 48 hours. After the completion of culture, 50 μL of the NITE BP-02779 culture solution and 5.0 mL of the excess sludge (killed bacteria)-containing inorganic medium were added to a test tube for reaction at 25° C. and 200 rpm, then the turbidity (OD660) of the test tube was measured over time with an easy operation turbidity meter (easy operation OD monitor miniphoto 518R, manufactured by TAITEC Corporation). The number of days required for the excess sludge (killed bacteria)-containing inorganic medium to exhibit the turbidity (OD660) that was 50% of the turbidity (OD660) of negative control was calculated. As the negative control, the turbidity (OD660) of a target bacterium (killed bacteria)-containing inorganic medium not supplemented with NITE BP-02779 was used.

(Results)

When NITE BP-02779 was added, decreases in the turbidity of excess sludge (killed bacteria) were observed, and the turbidity of excess sludge decreased to 50% of the turbidity of the negative control on day 3.2. Thus, NITE BP-02779 was capable of degrading the excess sludge (killed bacteria).

Experiment 4. Degradation Ability Evaluation of NITE BP-02779 on Excess Sludge (Killed Bacteria)-2

(Materials)

The same materials as in Experiment 3 were used.

(Method)

A reaction was carried out by the same method as in Experiment 3. The quintuplicate reaction was serially carried out, and the total amount of excess sludge that had remained in a test tube was collected on day 4 after the start of the reaction. The collected excess sludge was dried, and then the dried excess sludge was weighed to carry out the significance test (t-test, one-sided) between the negative control group and the NITE BP-02779 addition group.

(Results)

Figure 2:
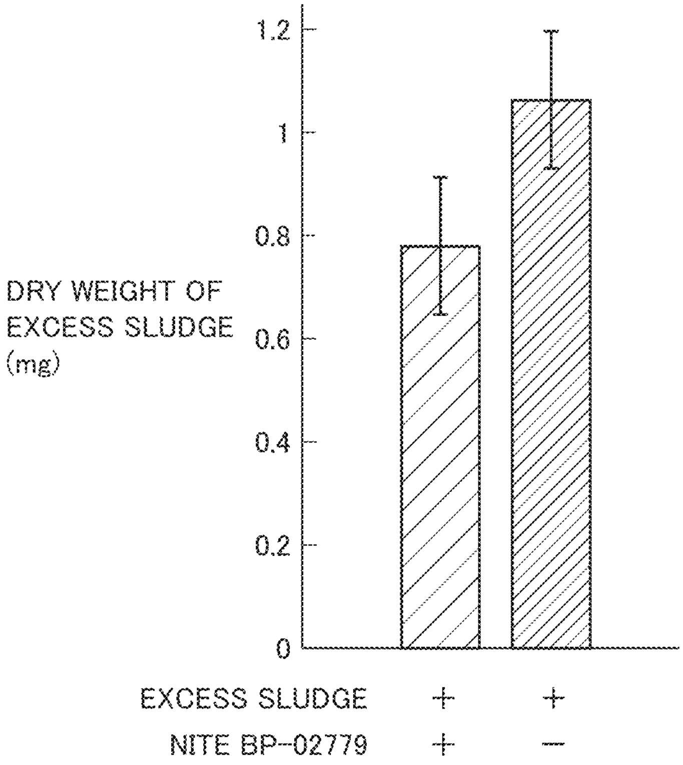
FIG. 2 is a chart showing a dry weight of excess sludge after addition of *Tumebacillus* sp. NITE BP-02779 in Experiment 4.

The results are shown in FIG. 2. A significant decrease ($p<0.01$) in the dry weight of excess sludge was observed for the NITE BP-02779 addition group in comparison with the negative control group. Thus, the excess sludge was reducible by the addition of NITE BP-02779.

Experiment 5. Determination of the Genomic Sequence of NITE BP-02779

(Method)

The genomic sequence of NITE BP-02779 was analyzed using a next generation sequencer by the following procedures. NITE BP-02779 was inoculated in 50 mL of R2A medium, followed by two days of shake culture at 25° C. and 130 rpm. The thus obtained cells were collected by centrifugation, and then the genomic DNA was extracted using a genomic DNA extraction kit (QIAamp DNA Mini Kit (250), manufactured by QIAGEN). Sequencing was carried out by the Paired-End method using the extracted DNA as a template and a next generation sequencer HiSeq 2500 (manufactured by Illumina, Inc.). Next an adapter sequence was trimmed from the obtained nucleotide sequence, and then de novo assembly was carried out using Velvet. Scaffold sequences obtained by de novo assembly were analyzed, and then gene region prediction and annotation were carried out. Rapid Annotations using Subsystems Technology (RAST) were used for gene region prediction and anotation.

(Results)

As a result of de novo assembly, 149 scaffolds were obtained and the total length of scaffold sequences was 4.44 Mbp, so that the presence of 4446 genes was predicted.

Experiment 6. Identification of Protein (ID2839) Having Peptidoglycan-Degrading Activity (1) Preparation of NITE BP-02779 culture supernatant (Method)

NITE BP-02779 was inoculated in 5 mL of R2A medium, and then preculture was carried out at 25° C. The thus obtained preculture solution (5 mL) was inoculated in 1.5 L of R2A medium, and then subjected to shake culture at 25° C. and 130 rpm. After 48 hours, the culture solution was centrifuged (4° C., 8000×g, 10 minutes), and then the obtained culture supernatant was filtered with a filter (0.20 μm). The filtered culture supernatant was concentrated using a centrifugal filter unit (manufactured by Merck Millipore), and then the resultant was used as a starting material for enzyme purification.

(2) Fractionation by Column Chromatography

Fractionation and purification of enzymes were carried out by the following column chromatography (a) to (c). The peptidoglycan-degrading activity of each fractionated fraction was measured using a Lysozyme activity kit (manufactured by Sigma-Aldrich). Proteins contained in the obtained fractions were electrophoresed on 4 to 20% Mini-PROTEAN TGX precast gels (manufactured by Bio-Rad Laboratories, Inc.) and then confirmed by CBB staining.

(a) Cation Exchange Chromatography (Materials)

Sample: concentrated solution of NITE BP-02779 culture supernatant (Method)

With the use of a centrifugal filter unit (manufactured by Merck Millipore), the buffer solution in a sample was exchanged with a 50 mM phosphate buffer solution (pH5.8). This sample was applied to a HiTrap Q HP, 5 mL column (manufactured by GE Healthcare) equilibrated using the buffer solution, the column was washed with the buffer solution, and then adsorbed proteins were eluted using a linear sodium chloride gradient from 0 to 1.0 M.

(Results)

When peptidoglycan-degrading activity was investigated, an unadsorbed fraction demonstrated the activity. Hence, the unadsorbed fraction was subjected to hydrophobic interaction chromatography.

(b) Hydrophobic Interaction Chromatography

Sample: Unadsorbed fraction of cation exchange chromatography (Method)

With the use of a centrifugal filter unit (manufactured by Merck Millipore), a buffer solution in the unadsorbed fraction of (a) cation exchange chromatography was exchanged with a 50 mM phosphate buffer solution (pH5.8) containing 1M ammonium sulfate. This sample was applied to a Hitrap HIC, 5 mL column (manufactured by GE Healthcare) equilibrated using the buffer solution. After the column was washed with the buffer solution, adsorbed proteins were eluted using a linear ammonium sulfate gradient from 1.0 to 0 M.

(Results)

When peptidoglycan-degrading activity was investigated, an adsorbed fraction demonstrated the activity. Hence, the fraction that had demonstrated activity was subjected to gel filtration chromatography.

(c) Gel Filtration Chromatography

Sample: Adsorbed fraction of hydrophobic interaction chromatography (Method)

With the use of a centrifugal filter unit (manufactured by Merck Millipore), the buffer solution in the adsorbed fraction of (b) hydrophobic interaction chromatography was exchanged with 66 mM potassium phosphate (pH6.24). The sample was applied to Superdex™ 75 10/300 GL (manufactured by GE Healthcare) equilibrated using the buffer solution for elution with the buffer solution.

(Results)

Figure 3:
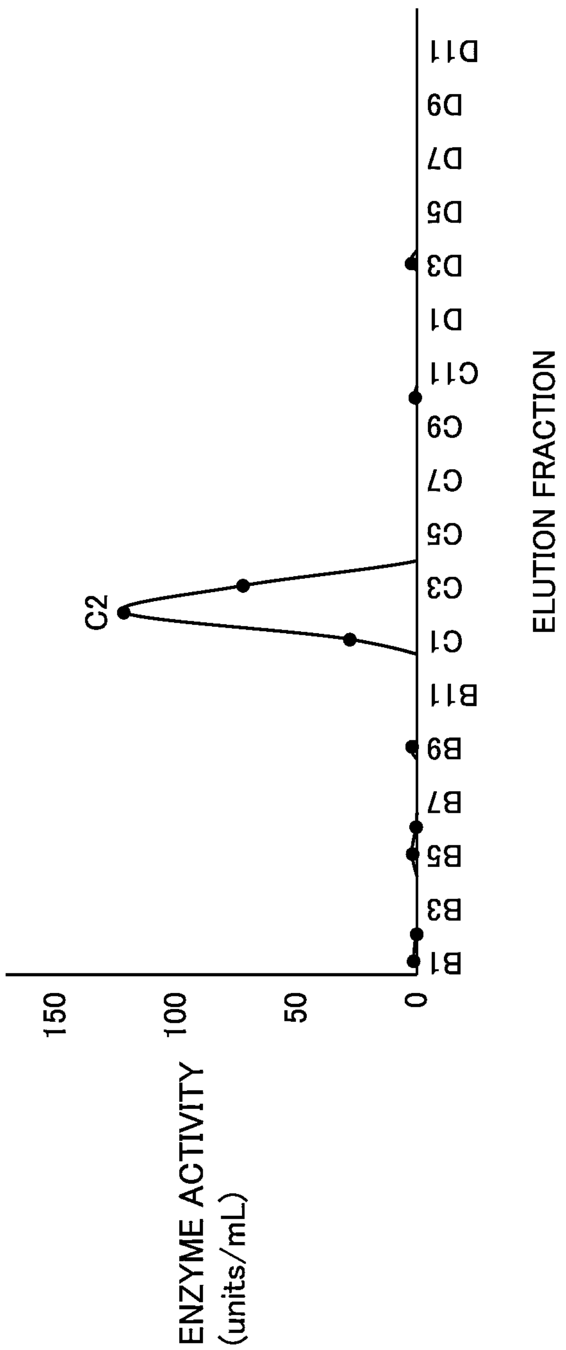
FIG. 3 is a chart showing the results of fractionating the culture supernatant of *Tumebacillus* sp. NITE BP-02779 by column chromatography to investigate the peptidoglycan-degrading activity in Experiment 6.

When peptidoglycan-degrading activity was investigated, as shown in FIG. 3, the elution fraction demonstrated the activity.

(3) Identification of Protein Having Peptidoglycan-Degrading Activity by Mass Spectrometry (Material)

Sample: Elution fraction of gel filtration chromatography (Method)

Figure 4:
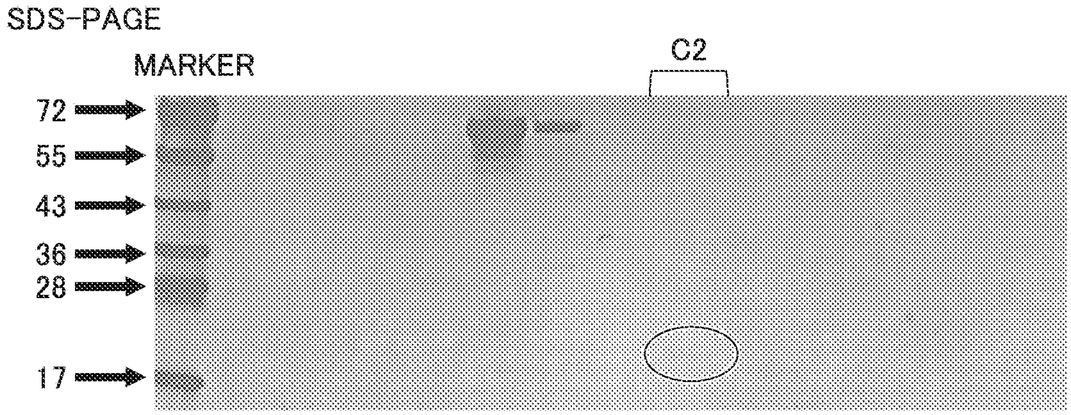
FIG. 4 shows the results of fractionating the culture supernatant of *Tumebacillus* sp. NITE BP-02779 by column chromatography and then detecting a protein contained in the elution fraction by electrophoresis in Experiment 6.

The elution fraction that had demonstrated the activity was concentrated using a centrifugal filter unit (manufactured by Merck Millipore), and then the resultant was electrophoresed on 4 to 20% Mini-PROTEAN TGX precast gels (manufactured by Bio-Rad Laboratories, Inc.). As a result, as shown in FIG. 4, the band derived from the protein contained in the elution fraction was confirmed to be a single band. The purified fraction of (c) gel filtration chromatography and the band separated by electrophoresis were each subjected to liquid phase digestion or in-gel digestion using trypsin, and then digested solutions were desalinated. The desalinated samples were subjected to Data Dependent MS/MS Acquisition (DDA) measurement using nano LC-MS (manufactured by Thermo Scientific, Q Exactive HF, nano column: Acclaim PepMap RSLC C18 (manufactured by Thermo Scientific)). After measurement, Mascot search (MS/MS ion search) was carried out on the protein sequence database prepared from the genome information of NITE BP-02779 using Proteome Discoverer 2.1.

(Results)

When a search for a trypsin cleaved peptide detected by mass spectrometry was carried out, the amino acid sequences of SEQ ID NOS: 11 to 17, which are partial sequences of ID2839, were detected. These partial sequences correspond to portions of the amino acid sequence at positions 15 to 164 of SEQ ID NO: 2. The above result suggested that protein ID2839 expressed by NITE BP-02779 has peptidoglycan-degrading activity.

(4) Identification of the N-Terminal Cleavage Site of ID2839

(Method)

Further, DDA measurement data file, with which ID2839 had been identified, was searched for a peptide to confirm if it contained the peptide cleaved at an arbitrary site on the N-terminal side between positions −11 and 14 of SEQ ID NO: 2.

(Results)

A partial sequence of SEQ ID NO: 18 was obtained as a peptide having the highest signal intensity. The partial sequence of SEQ ID NO: 18 corresponds to positions 1 to 10 of SEQ ID NO: 2. Accordingly, the entire amino acid sequence of SEQ ID NO: 2 was considered to be the amino acid sequence of an ID2839 precursor (pro-sequence). The amino acid sequence of the ID2839 mature body corresponds to positions 1 to 164 of SEQ ID NO: 2, and is considered to be encoded by the nucleotide sequence at positions 205 to 696 of SEQ ID NO: 1. Positions −68 to −1 of SEQ ID NO: 2 are considered to be a signal peptide. Hereinafter, the protein consisting of the amino acid sequence at positions 1 to 164 of SEQ ID NO: 2 may be referred to as "ID2839 mature body", and the protein consisting of the entire amino acid sequence (positions −68 to 164) of SEQ ID NO: 2 may be referred to as "ID2839 precursor". It is considered that the signal peptide is cleaved from ID2839 precursor to yield ID2839 mature body, and then ID2839 mature body is secreted extracellularly, and becomes capable of degrading peptidoglycan. The molecular weight of ID2839 precursor was about 25 kDa and the molecular weight of ID2839 mature body was about 18 kDa.

Experiment 7. Measurement of Specific Activity of ID2839 Mature Body (Material)

ID2839 mature body (elution fraction of gel filtration chromatography)

(Method)

ID2839 mature body was subjected to activity measurement (Units/mL) and protein quantification (mg/mL), so that specific activity (Units/mg) was calculated. Commercially available 2 types of lytic enzymes (manufactured by Sigma-Aldrich) were used as control. Using a lysozyme activity kit (manufactured by Sigma-Aldrich), peptidoglycan-degrading activity was evaluated in terms of the activity to degrade a glycosidic linkage between N-acetylmuramic acid and N-acetylglucosamine.

(Results)

The results are shown in Table 5. It was demonstrated that ID2839 mature body has the activity to degrade a glycosidic linkage between N-acetylmuramic acid and N-acetylglucosamine, and the specific activity is higher than that of commercially available Mutanolysin or Lysostaphin.

TABLE 5

| Specimen | Specific activity(Units/mg) |
|---|---|
| ID2839 mature body | 78717 |
| Mutanolysin (manufactured by Sigma-Aldrich) | 305 |
| Lysostaphin (manufactured by Sigma-Aldrich) | 294 |

Experiment 8. Preparation of ID2839 Mature Body in *E. coli*

(1) Construction of ID2839 Mature Body Expression Strain
(Materials)

Primers F and R for cloning ID2839 (SEQ ID NOS: 19 and 20)

LB agar medium: Agar medium obtained by dissolving LB Ager (manufactured by Sigma-Aldrich) in a proportion of 10 pieces relative to 500 mL of ultrapure water and autoclaving the solution, followed by dispensation into a dish (Method)

A region containing the nucleotide sequence encoding ID2839 mature body (Ala at position 1 was substituted with Met in SEQ ID NO: 2) was amplified by PCR using the genomic DNA of NITE BP-02779 as a template, and primers F and R for cloning ID2839. PCR amplification was carried out using KOD FX (manufactured by TOYOBO CO., LTD.). The reaction solution was prepared according to the composition attached to the kit, and the reaction was carried out under conditions of (1) 94° C., 2 minutes, (2) 98° C., 10 seconds, (3) 50° C., 30 seconds, and (4) 68° C., 1.5 minutes, wherein steps (2) to (4) were carried out repeatedly for 25 cycles. The thus obtained PCR fragment and a pET-28a(+) vector (manufactured by Merck Millipore) were each digested with NdeI and XhoI, and then ligated using ligation high Ver. 2 (manufactured by TOYOBO CO., LTD.). *E. coli* DH5a was transformed with the ligation reaction solution, a plasmid of interest was extracted from kanamycin resistant strains. *E. coli* BL21(DE3) was transformed using the plasmid, thereby obtaining an ID2839 mature body expression strain (also referred to as "BL21(DE3)/pET28a-ID2839 mature body"). In BL21(DE3)/pET28a-ID2839 mature body, a protein, in which the amino acid sequence containing a His tag and a thrombin cleavage site (MetGlySerSerHisHisHisHisHisHisSerSerGlyLeuValProArgGlySerHis: SEQ ID NO: 21) had been added to the N-terminus of mature protein (Ala at position 1 was substituted with Met in SEQ ID NO: 2), is expressed. A strain (also referred to as "BL21(DE3)/pET28a") not expressing ID2839 mature body was also obtained as a control strain.

(2) Induction of Expression of ID2839 Mature Body and Preparation of Soluble Fraction
(Materials)

LB liquid medium: Medium obtained by dissolving LB Broth, 1. 1G PER TABLET (manufactured by Sigma-Aldrich) in a proportion of 10 pieces relative to 500 mL of ultrapure water and being autoclaved.

Transformant: BL21 (DE3)/pET28a-ID2839 mature body

Transformant (control):BL21(DE3)/pET28a (Method)

Each transformant strain was inoculated in 5 mL of LB medium containing kanamycin at 50 mg/L and then subjected to preculture at 37° C. The thus obtained preculture solution (1.0 mL) was inoculated in 100 mL of LB medium containing kanamycin at 50 mg/L, and then subjected to shake culture using baffled flasks. When OD660 reached 0.6, IPTG was added (final concentration: 0.1 mM), followed by 16 hours of culture at 18° C. After the completion of culture, cells were collected from the obtained culture solution by centrifugation, BugBuster (manufactured by Novagen) was added in a certain amount per wet cell weight, so as to disrupt cells. Cell residues were removed from the cell-disrupted solution by centrifugation, thereby obtaining supernatants as soluble fractions. A soluble fraction containing ID2839 mature body was obtained from BL21(DE3)/pET28a-ID2839 mature body. A soluble fraction not containing ID2839 mature body was obtained from BL21(DE3)/pET28a.

(3) Activity Evaluation on Soluble Fraction
(Materials)

BL21(DE3)/pET28a-ID2839 mature body-derived soluble fraction

BL21(DE3)/pET28a-derived soluble fraction (Method)

Using a lysozyme activity kit (manufactured by Sigma-Aldrich), the activity (Units/mL) to degrade a glycosidic linkage between N-acetylmuramic acid and N-acetylglucosamine was calculated. The activity (UNITS/mL) was calculated using the following formula.

Activity to degrade glycosidic linkage between N-acetylmuramic acid and N-acetylglucosamine (UNITS/mL)={ΔABS450 nm/min (target bacterium-containing phosphate buffer solution supplemented with soluble fraction)−ΔABS450 nm/min (target bacterium-containing phosphate buffer solution not supplemented with soluble fraction)}/(0.001×0.1)

(Results)

The results are shown in Table 6. BL21(DE3)/pET28a-ID2839 mature body-derived soluble fraction was observed to demonstrate the activity to degrade a glycosidic linkage between N-acetylmuramic acid and N-acetylglucosamine, but control BL21(DE3)/pET28a-derived soluble fraction was almost not observed to demonstrate the activity to degrade a glycosidic linkage between N-acetylmuramic acid and N-acetylglucosamine. It was found that ID2389 mature body has peptidoglycan-degrading activity and has the activity to degrade a glycosidic linkage between N-acetylmuramic acid and N-acetylglucosamine.

TABLE 6

| Sample | Activity(Units/mL) |
|---|---|
| BL21(DE3)/pET28a-ID2839 mature body | 264 |
| BL21(DE3)/pET28a | 0 |

Experiment 9. Identification of Protein (ID1644) Having Peptidoglycan-Degrading Activity (1) Identification from Genome Information The gene of an enzyme having high identity to N-acetylmuramoyl-L-alanineamidase was found from the result of decoding the genomic sequence of NITE BP-02779. This enzyme was named ID1644. ID1644 was secreted in the culture supernatant of NITE BP-02779. The entire amino acid sequence of SEQ ID NO: 4 was considered to be the amino acid sequence of a precursor (pro sequence). The amino acid sequence of the mature protein is at positions 1 to 493 of SEQ ID NO: 4, and was considered to be encoded by the nucleotide sequence at positions 85 to 1.563 of SEQ ID NO: 3. Positions −28 to −1 of SEQ ID NO: 4 were considered to be a signal peptide. Hereinafter, the protein consisting of the amino acid sequence at positions 1 to 493 of SEQ ID NO: 4 may be referred to as "ID1644 mature body" and the protein consisting of the entire amino acid sequence (positions −28 to 493) of SEQ ID NO: 4 may be referred to as "ID1644 precursor". It is considered that the signal peptide is cleaved from ID precursor to yield ID1644 mature body, and then ID1644 mature body is secreted extracellularly, so as to be able to degrade peptidoglycan.

The molecular weight of ID precursor was about 56 kDa and the molecular weight of ID1644 mature body was about 53 kDa.

Experiment 10. Preparation of ID Mature Body in *E. coli*

(1) Construction of ID1644 mature body expression strain (Materials)

Primers F and R for cloning ID1644 (SEQ ID NO: 22 and 23)

LB agar medium (Method)

A region containing the nucleotide sequence encoding ID1644 mature body was amplified by PCR using the genomic DNA of NITE BP-02779 as a template and primers F and R for cloning ID1644. PCR amplification was carried out using KOD FX (manufactured by TOYOBO CO., LTD.). The reaction solution was prepared according to the composition attached to the kit, and the reaction was carried out under conditions of (1) 94° C., 2 minutes, (2) 98° C., 10 seconds, (3) 50° C., 30 seconds, and (4) 68° C., 1.5 minutes, wherein steps (2) to (4) were repeatedly carried out for 25 cycles. The thus obtained PCR fragment and a pET-22b(+) vector (manufactured by Merck Millipore) were each digested with NdeI and XhoI, and then ligated using ligation high Ver. 2 (manufactured by TOYOBO CO., LTD.). *E. coli* DH5a was transformed with the ligation reaction solution, and then a plasmid of interest was extracted from ampicillin-resistant strains. *E. coli* BL21(DE3) was transformed using the plasmid, thereby obtaining an ID mature body expression strain (also referred to as "BL21(DE3)/pET22b-ID1644 mature body"). In the case of BL21(DE3)/pET22b-ID1644 mature body, a protein, in which methionine had been added to the N-terminus of the mature protein (positions 1 to 493 of SEQ ID NO: 4), is expressed. A strain not expressing ID1644 mature body (also referred to as "BL21(DE3)/pET22b") was also obtained as a control strain.

(2) Induction of Expression of ID1644 Mature Body and Preparation of Soluble Fraction (Materials)

LB liquid medium

Transformant: BL21(DE3)/pET22b-ID1644 mature body

Transformant (control): BL21(DE3)/pET22b (Method)

Each transformant strain was inoculated in 5 mL of LB medium containing ampicillin at 100 mg/L, and then subjected to preculture at 37° C. The thus obtained preculture solution (1.0 mL) was inoculated in 100 mL of LB medium containing ampicillin at 100 mg/L, and then subjected to shake culture using baffled flasks. When OD660 reached 0.6, IPTG was added (final concentration: 0.1 mM), followed by 16 hours of culture at 18° C. After the completion of culture, cells were collected from the obtained culture solution by centrifugation, BugBuster (manufactured by Novagen) was added in a certain amount per wet cell weight, so as to disrupt cells. Cell residues were removed from the cell-disrupted solution by centrifugation, thereby obtaining a supernatant as a soluble fraction. A soluble fraction containing ID1644 mature body was obtained from BL21(DE3)/pET22b-ID1644 mature body. A soluble fraction not containing ID1644 mature body was obtained from BL21(DE3)/pET22b.

(3) Activity Evaluation on Soluble Fraction −1

(Materials)

BL21(DE3)/pET22b-ID1644 mature body-derived soluble fraction

BL21(DE3)/pET22b-derived soluble fraction

Peptidoglycan solution: Solution obtained by dissolving peptidoglycan (manufactured by Sigma-Aldrich) in a proportion of 10 mg per 50 mL of the phosphate buffer solution (pH 7.0).

(Method)

A peptidoglycan solution (5 mL) and 50 μL of a soluble fraction were mixed, and then OD450 was measured over time, thereby calculating peptidoglycan-degrading activity (Units/mL). The peptidoglycan-degrading activity (UNITS/mL) was calculated using the following formula.

Peptidoglycan-degrading activity (UNITS/mL) ={ΔABS450 nm/min (peptidoglycan-containing phosphate buffer solution supplemented with soluble fraction)−ΔABS450 nm/min (peptidoglycan-containing phosphate buffer solution not supplemented with soluble fraction)}/(0.001×0.05)

(Results)

The results are shown in Table 7. BL21(DE3)/pET22b-ID1644 mature body-derived soluble fraction was observed to demonstrate peptidoglycan-degrading activity, but control BL21(DE3)/pET22b-derived soluble fraction was not observed to demonstrate peptidoglycan-degrading activity. ID1644 mature body was found to have peptidoglycan-degrading activity.

TABLE 7

| Sample | Activity(Units/mL) |
|---|---|
| BL21(DE3)/pET22b-ID1644 mature body | 100 |
| BL21(DE3)/pET22b | 2 |

(4) Activity Evaluation on Soluble Fraction −2

(Materials)

BL21(DE3)/pET22b-ID1644 mature body-derived soluble fraction

BL21(DE3)/pET22b-derived soluble fraction

Substrate for N-acetylmuramoyl-L-alanineamidase: L-aniline-p-nitroanilide hydrochloride (manufactured by Sigma-Aldrich)

(Method)

A soluble fraction (10 μL), 10 μL of a lmg/mL substrate solution, and 80 μL of a 100 mM Tris-HCl (pH7.6) were left to stand at 37° C. for 10 minutes, and then the absorbance (405 nm) was measured using a microplate reader (manufactured by Molecular Device).

(Results)

The results are shown in Table 8. BL21(DE3)/pET22b-ID1644 mature body-derived soluble fraction exhibited ABS at 405 nm higher than that of BL21(DE3)/pET22b-derived soluble fraction. ID1644 mature body was found to have the activity of N-acetylmuramoyl-L-alanineamidase.

TABLE 8

| Sample | ABS405 nm |
|---|---|
| BL21(DE3)/pET22b-ID1644 mature body | 0.536 |
| BL21(DE3)/pET22b | 0.142 |

Experiment 11. Preparation of ID2839 Mature Body-2 in *E. coli*

(1) Construction of ID2839 Mature Body-2 Expression Strain s(Materials)

Primers F and R for cloning ID2839 (SEQ ID NOS: 24 and 25)

LB agar medium (Method)

A region containing a nucleotide sequence encoding ID2839 mature body-2 (the protein consisting of the amino acid sequence at positions 1 to 164 of SEQ ID NO: 2 with addition of Met to the N-terminus of Ala at position 1) was amplified by PCR using the genomic DNA of NITE BP-02779 as a template and primers for cloning ID2839 (SEQ ID NOS: 24 and 25). PCR amplification was carried out using KOD plus NEO (manufactured by TOYOBO CO., LTD.). The reaction solution was prepared according to the composition attached to the kit. PCR was carried out under conditions of (1) 94° C., 2 minutes, (2) 98° C., 10 seconds, and (3) 68° C., 30 seconds, wherein the steps (2) and (3) were carried out repeatedly for 30 cycles. The thus obtained PCR fragment and a fragment obtained by digestion of pET-28a(+) vector (manufactured by Merck Millipore) with NcoI and XhoI were ligated using an In-Fusion HD Cloning Kit (manufactured by TAKARA BIO INC.). *E. coli* DH5α was transformed with the ligation reaction solution, and then a plasmid of interest was extracted from kanamycin resistant strains. *E. coli* BL21(DE3) was transformed using the plasmid, thereby obtaining an ID2839 mature body-2 expression strain (also referred to as "BL21(DE3)/pET28a-ID2839 mature body-2"). In BL21(DE3)/pET28a-ID2839 mature body-2, the mature protein (the protein consisting of the amino acid sequence at positions 1 to 164 of SEQ ID NO: 2 with addition of Met to the N-terminus of Ala at position 1) is expressed.

(2) Induction of Expression of ID2839 Mature Body-2 and Preparation of Soluble Fraction (Materials)

LB liquid medium

Transformant: BL21(DE3)/pET28a-ID2839 mature body-2

Transformant (control): BL21(DE3)/pET28a (Method)

Each transformant strain was inoculated in 5 mL of LB medium containing kanamycin at 50 mg/L, and then subjected to preculture at 37° C. The thus obtained preculture solution (1.0 mL) was inoculated in 100 mL of LB medium containing kanamycin at 50 mg/L, and then subjected to shake culture using baffled flasks. When OD660 reached 0.6, IPTG was added (final concentration: 1 mM), followed by 20 hours of culture at 24° C. After completion of culture, soluble fractions of cells were obtained in the same manner as in Experiment 8.

(3) Activity Evaluation on Soluble Fraction (Materials)

BL21(DE3)/pET28a-ID2839 mature body-2-derived soluble fraction

BL21(DE3)/pET28a-derived soluble fraction (Method)

Activity evaluation was carried out in the same manner as in Experiment 8.

(Results)

The results are shown in Table 9. BL21(DE3)/pET28a-ID2839 mature body-2 soluble fraction was observed to demonstrate peptidoglycan-degrading activity.

TABLE 9

| Sample | Activity(Units/mL) |
|---|---|
| BL21(DE3)/pET28a-ID2839 mature body-2 | 65.1 |
| BL21(DE3)/pET28a | 0 |

Experiment 12. Preparation of ID2839 Mature Body-3 in *E. coli*

(1) Construction of ID2839 Mature Body-3 Expression Strain (Materials)

Primers F and R for cloning ID2839 (SEQ ID NOS: 26 and 25)

LB agar medium (Method)

Except of using the primers for cloning represented by SEQ ID NO: 26 and 25, an ID2839 mature body-3 expression strain (also referred to as "BL21(DE3)/pET28a-ID2839 mature body-3") was obtained in the same manner as in Experiment 11. In BL21(DE3)/pET28a-ID2839 mature body-3, the mature protein (the protein consisting of the amino acid sequence at positions 1 to 164 of SEQ ID NO: 2 with a substitution of Ala at position 1 with Met) is expressed.

(2) Induction of Expression of ID2839 Mature Body and Preparation of Soluble Fraction (Materials)

LB liquid medium

Transformant: BL21(DE3)/pET28a-ID2839 mature body-3

Transformant (control): BL21(DE3)/pET28a (Method)

Soluble fractions of cells were obtained in the same manner as in Experiment 11.

(3) Activity Evaluation on Soluble Fraction (Materials)

BL21(DE3)/pET28a-ID2839 mature body-3-derived soluble fraction

BL21(DE3)/pET28a-derived soluble fraction (Method)

Activity evaluation was carried out in the same manner as in Experiment 8.

(Results)

The results are shown in Table 10. BL21(DE3)/pET28a-ID2839 mature body-3-derived soluble fraction was observed to demonstrate peptidoglycan-degrading activity.

TABLE 10

| Sample | Activity (Units/mL) |
|---|---|
| BL21(DE3)/pET28a-ID2839 mature body-3 | 79.0 |
| BL21(DE3)/pET28a | 0 |

The invention claimed is:

1. A method for degrading a microorganism, comprising allowing at least one selected from the group consisting of:

a transformant comprising a DNA encoding a protein derived from *Tumebacillus* sp. NITE BP-02779 and having peptidoglycan-degrading activity; and a culture thereof which includes a transformant comprising a DNA encoding a protein derived from *Tumebacillus* sp. NITE BP-02779 and having peptidoglycan-degrading activity;

to act on a target microorganism;

wherein the protein is any one of the following proteins (A1) to (A3) or (B1) to (B3):

(A1) a protein comprising the amino acid sequence at positions 1 to 164 of SEQ ID NO: 2, and having peptidoglycan-degrading activity;

(A2) a protein comprising the amino acid sequence at positions 1 to 164 of SEQ ID NO: 2 with a substitution, deletion, insertion or addition of 1 to 10 amino acid residues, and having peptidoglycan-degrading activity;

(A3) a protein comprising an amino acid sequence having 93% or more identity to the amino acid sequence at positions 1 to 164 of SEQ ID NO: 2, and having peptidoglycan-degrading activity;

(B1) a protein comprising the amino acid sequence at positions 1 to 493 of SEQ ID NO: 4, and having peptidoglycan-degrading activity;

(B2) a protein comprising the amino acid sequence at positions 1 to 493 of SEQ ID NO: 4 with a substitution, deletion, insertion or addition of 1 to 10 amino acid residues, and having peptidoglycan-degrading activity; and (B3) a protein comprising an amino acid sequence having 93% or more identity to the amino acid sequence at positions 1 to 493 of SEQ ID NO: 4,and having peptidoglycan-degrading activity, wherein the target microorganism has peptidoglycan.

2. A method for degrading a microorganism, comprising allowing at least one selected from the group consisting of:

a transformant comprising a vector comprising a DNA encoding a protein derived from *Tumebacillus* sp. NITE BP-02779 and having peptidoglycan-degrading activity; and a culture thereof which includes a transformant comprising a vector comprising a DNA encoding a protein derived from *Tumebacillus* sp. NITE BP-02779 and having peptidoglycan- degrading activity;

to act on a target microorganism;

wherein the protein is any one of the following proteins (A1) to (A3) or (B1) to (B3):

(A1) a protein comprising the amino acid sequence at positions 1 to 164 of SEQ ID NO: 2, and having peptidoglycan-degrading activity;

(A2) a protein comprising the amino acid sequence at positions 1 to 164 of SEQ ID NO: 2 with a substitution, deletion, insertion or addition of 1 to 10 amino acid residues, and having peptidoglycan-degrading activity;

(A3) a protein comprising an amino acid sequence having 93% or more identity to the amino acid sequence at positions 1 to 164 of SEQ ID NO: 2, and having peptidoglycan-degrading activity;

(B1) a protein comprising the amino acid sequence at positions 1 to 493 of SEQ ID NO: 4, and having peptidoglycan-degrading activity;

(B2) a protein comprising the amino acid sequence at positions 1 to 493 of SEQ ID NO: 4 with a substitution, deletion, insertion or addition of 1 to 10 amino acid residues, and having peptidoglycan-degrading activity; and (B3) a protein comprising an amino acid sequence having 93% or more identity to the amino acid sequence at positions 1 to 493 of SEQ ID NO: 4, and having peptidoglycan-degrading activity, wherein the target microorganism has peptidoglycan.

3. The method according to claim 1, wherein the peptidoglycan-degrading activity is activity to degrade a glycosidic linkage between N-acetylmuramic acid and N-acetylglucosamine.

4. The method according to claim 1, wherein the protein according to (A1) further comprises:

(a1) a protein consisting of the amino acid sequence at positions 1 to 164 of SEQ ID NO: 2;

and wherein the protein according to (A2) further comprises any one of the following:

(a2) a protein consisting of the amino acid sequence at positions 1 to 164 of SEQ ID NO: 2 with a substitution of Ala at position 1 with Met;

(a3) a protein consisting of the amino acid sequence at positions 1 to 164 of SEQ ID NO: 2 with a substitution of Ala at position 1 with Met and addition of the amino acid sequence represented by SEQ ID NO: 21 to the N-terminus of the Met; and (a4) a protein consisting of the amino acid sequence at positions 1 to 164 of SEQ ID NO: 2 with addition of Met to the N-terminus of Ala at position 1.

5. The method according to claim 1, wherein the peptidoglycan-degrading activity is N-acetylmuramoyl-L-alanine amidase activity.

6. The method according to claim 1, wherein the protein is according to (B1) further comprises:

(b1) a protein consisting of the amino acid sequence at positions 1 to 493 of SEQ ID NO: 4;

and wherein the protein according to (B2) further comprises any one of the following:

(b2) a protein consisting of the amino acid sequence at positions 1 to 493 of SEQ ID NO: 4 with a substitution of Glu at position 1 with Met;

(b3) a protein consisting of the amino acid sequence at positions 1 to 493 of SEQ ID NO: 4 with a substitution of Glu at position 1 with Met and addition of the amino acid sequence represented by SEQ ID NO: 21 to the N-terminus of the Met; and (b4) a protein consisting of the amino acid sequence at positions 1 to 493 of SEQ ID NO: 4 with addition of Met to the N-terminus of Glu at position 1.

7. The method according to claim 1, wherein the target microorganism is a bacterium that is a component of excess sludge.

* * * * *